(12) United States Patent
Fraasch et al.

(10) Patent No.: US 12,303,184 B2
(45) Date of Patent: May 20, 2025

(54) METHODS OF ENSURING PULSED FIELD ABLATION GENERATOR SYSTEM ELECTRICAL SAFETY

(71) Applicant: Medtronic, Inc., Minneapolis, MN (US)

(72) Inventors: Steven J. Fraasch, Maple Grove, MN (US); Catherine R. Condie, Shoreview, MN (US); Brian T. Howard, Minneapolis, MN (US); Louis Jacob, Laval (CA); Paul S. Lam, Eden Prairie, MN (US); Trenton J. Rehberger, Minneapolis, MN (US); Mark T. Stewart, Lino Lakes, MN (US); Qin Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1245 days.

(21) Appl. No.: 17/078,367

(22) Filed: Oct. 23, 2020

(65) Prior Publication Data

US 2021/0038283 A1 Feb. 11, 2021

Related U.S. Application Data

(62) Division of application No. 15/418,217, filed on Jan. 27, 2017, now Pat. No. 10,849,677.

(51) Int. Cl.
*A61B 18/12* (2006.01)
*A61B 5/00* (2006.01)
(Continued)

(52) U.S. Cl.
CPC .......... *A61B 18/1233* (2013.01); *A61B 5/287* (2021.01); *A61B 5/349* (2021.01);
(Continued)

(58) Field of Classification Search
CPC ..... A61B 18/1233; A61B 5/287; A61B 5/349; A61B 5/352; A61B 5/746; A61B 18/1492;
(Continued)

(56) References Cited

U.S. PATENT DOCUMENTS 3,468,164 A 9/1969 Sutherland
4,375,074 A 2/1983 Glogolja
(Continued)

FOREIGN PATENT DOCUMENTS

CN 102361667 A 2/2012

OTHER PUBLICATIONS

Chinese Patent Office First Office Action for Application No. 201880008772.6 dated Apr. 2, 2022 (14 pages including English summary).

*Primary Examiner* — Linda C Dvorak
*Assistant Examiner* — Lindsay Regan Lancaster
(74) *Attorney, Agent, or Firm* — Michael Best & Friedrich LLP

(57) ABSTRACT

A system and method for the safe delivery of treatment energy to a patient, which includes verification of system integrity before, during, or after the delivery of treatment energy and provides several mechanisms for rapid termination of the delivery of potentially harmful energy to the patient when a fault condition in the device and/or system is identified. The system may include an energy generator having processing circuitry to determine if there is a fault condition in the system and to automatically terminate a delivery of treatment energy when the processing circuitry determines there is a fault condition. The method may generally include performing a series of pre-checks, synchronizing a treatment energy delivery to the proper segment of the heart's depolarization pattern, configuring the (Continued)

system for treatment energy delivery, delivering the treatment energy, and performing post-treatment evaluation.

17 Claims, 24 Drawing Sheets

(51) Int. Cl.
*A61B 5/287* (2021.01)
*A61B 5/349* (2021.01)
*A61B 5/352* (2021.01)
*A61B 18/14* (2006.01)
*A61N 1/30* (2006.01)
*H02H 1/00* (2006.01)
*H02H 3/16* (2006.01)
*A61B 18/00* (2006.01)
*A61B 18/16* (2006.01)

(52) U.S. Cl.
CPC .............. *A61B 5/352* (2021.01); *A61B 5/746* (2013.01); *A61B 18/1492* (2013.01); *A61N 1/303* (2013.01); *H02H 1/0007* (2013.01); *H02H 3/16* (2013.01); *A61B 2018/0016* (2013.01); *A61B 2018/00166* (2013.01); *A61B 2018/00214* (2013.01); *A61B 2018/00351* (2013.01); *A61B 2018/00357* (2013.01); *A61B 2018/00511* (2013.01); *A61B 2018/00541* (2013.01); *A61B 2018/00577* (2013.01); *A61B 2018/00613* (2013.01); *A61B 2018/00654* (2013.01); *A61B 2018/00666* (2013.01); *A61B 2018/00702* (2013.01); *A61B 2018/00708* (2013.01); *A61B 2018/00821* (2013.01); *A61B 2018/00839* (2013.01); *A61B 2018/00875* (2013.01); *A61B 2018/00892* (2013.01); *A61B 2018/00898* (2013.01); *A61B 2018/126* (2013.01); *A61B 2018/1266* (2013.01); *A61B 2018/1407* (2013.01); *A61B 2018/1467* (2013.01); *A61B 2018/1475* (2013.01); *A61B 18/16* (2013.01)

(58) Field of Classification Search
CPC ............ A61B 18/16; A61B 2018/0016; A61B 2018/00166; A61B 2018/00214; A61B 2018/00351; A61B 2018/00357; A61B 2018/00511; A61B 2018/00541; A61B 2018/00577; A61B 2018/00613; A61B 2018/00654; A61B 2018/00666; A61B 2018/00702; A61B 2018/00708; A61B 2018/00821; A61B 2018/00839; A61B 2018/00875; A61B 2018/00892; A61B 2018/00898; A61B 2018/126; A61B 2018/1266; A61B 2018/1407; A61B 2018/1467; A61B 2018/1475; A61N 1/303; H02H 1/0007; H02H 3/16

See application file for complete search history.

(56) References Cited

U.S. PATENT DOCUMENTS

| | | | |
|---|---|---|---|
| 5,642,247 A * | 6/1997 | Giordano | ............ H02H 7/0838 |
| | | | 318/434 |
| 5,830,212 A * | 11/1998 | Cartmell | ............ A61B 18/1233 |
| | | | 128/908 |
| 8,007,494 B1 | 8/2011 | Taylor et al. | |
| 8,251,989 B1 | 8/2012 | Newton | |
| 9,956,027 B2 | 5/2018 | Newton | |
| 2003/0097125 A1 | 5/2003 | Hall | |
| 2003/0204185 A1 | 10/2003 | Sherman | |
| 2004/0030328 A1 | 2/2004 | Eggers et al. | |
| 2008/0172050 A1 | 7/2008 | Satake | |
| 2009/0112204 A1 | 4/2009 | Aronow et al. | |
| 2010/0049188 A1 * | 2/2010 | Nelson | ............... A61B 18/1492 |
| | | | 606/34 |
| 2013/0324993 A1 * | 12/2013 | McCarthy | ................ A61B 5/01 |
| | | | 606/33 |
| 2013/0336356 A1 * | 12/2013 | Martin | ............... A61B 18/1206 |
| | | | 374/45 |
| 2014/0276754 A1 | 9/2014 | Gilbert | |
| 2015/0116884 A1 * | 4/2015 | Santana | ................... H02H 3/08 |
| | | | 361/103 |
| 2015/0320478 A1 | 11/2015 | Cosman, Jr. et al. | |
| 2015/0359584 A1 | 12/2015 | Newton | |

* cited by examiner

METHODS OF ENSURING PULSED FIELD ABLATION GENERATOR SYSTEM ELECTRICAL SAFETY

CROSS-REFERENCE TO RELATED APPLICATION

This application is a divisional of and claims the benefit of U.S. application Ser. No. 15/418,217, filed Jan. 27, 2017.

STATEMENT REGARDING FEDERALLY SPONSORED RESEARCH OR DEVELOPMENT n/a

TECHNICAL FIELD

The present invention relates to a method and system for protective measures applied to energy generators.

BACKGROUND

Cardiac arrhythmias disrupt the normal heart rhythm and cardiac efficiency. These arrhythmias can be treated using the application of treatment energy, such as pulsed electric field ablation (PFA) energy, radiofrequency (RF) energy, pulsed RF energy, ultrasound energy, and the like, and/or by removing heat from the tissue through cryotreatment. During a PFA procedure, safe and effective treatment requires that the system generating and delivering the high level electrical energy be in good operating condition.

In the case of a PFA energy generator electrical failure, potential hazards to the patient may be created. While medical equipment standards (for example, those established by the International Electrotechnical Commission, IEC) limit inadvertent patient current to less than 10 microamps (1e-5 amps), the application of direct current (DC), on the order of 10 milliamps or more but no more than 100 amps, from a PFA energy generator would cause electrocution, either by inducing a severely held ventricular contraction, by inducing ventricular fibrillation, or by causing thermal damage to the heart. Other dangers may include the induction of a thermal emboli-induced ischemic cerebral injury or inadvertent thermal damage to tissues if the generator fails to terminate its waveform and "runs on" or if the delivered current is too high.

Another hazard is presented when the PFA energy waveform is no longer symmetric and biphasic, but instead becomes monophasic. In this case, a large amount of charge (for example, as high as 4 Coulombs) is delivered to the patient via the catheter or medical device within the patient's body. This causes extreme muscular stimulation accompanied by severe pain and violent movement. Further, the imparting of charge can complicate an electrophysiology assessment, particularly of local intracardiac electrogram (EGM) signals, potentially prolonging procedure times.

In these cases, it is imperative to monitor the delivered waveform current and remove treatment energy when the temperature or rate of temperature change is too high or other indications of fault are detected. Unless detected and corrected instantly by active safeguards, these patient risks may be unacceptably high.

Assuming that active monitoring and safeguards are in place, the problems of how to communicate the commands within the electronic infrastructure, how to report faults, and how to recommend the user's corrective action still remain. For example, a generator fault may require a simple action of recycling power, or an action that is more critical, such as requiring that the generator be replaced. Another fault may appear to occur in the generator, when in fact the fault occurs elsewhere in the system, such as in a cable or treatment device. Therefore, it is important to provide the user with clear guidance for correcting faults quickly, especially if the treatment procedure would be unduly lengthened by attempting to blindly troubleshoot an inoperative energy delivery system.

SUMMARY

The present invention advantageously provides a system and method for the safe delivery of treatment energy to a patient, which includes verification of device and/or system integrity before, during, or after the delivery of treatment energy and providing several mechanisms, both primary and redundant, for rapid termination of the delivery of potentially harmful energy to the patient when a fault condition in the device and/or system is identified.

In one embodiment, a medical system may include a medical device including a treatment element having a plurality of electrodes; an energy generator in communication with the plurality of electrodes, the energy generator including: processing circuitry to determine if there is a fault condition in the system and to automatically terminate a delivery of treatment energy when the processing circuitry determines there is a fault condition; and at least one relay configured to selectively interrupt the communication between the energy generator and the plurality of electrodes when the processing circuitry determines there is a fault condition. The system may further include a catheter electrode distribution system (CEDS) in communication with the energy generator and the plurality of electrodes, the CEDS including at least one relay configured to selectively interrupt the communication between the energy generator and the plurality of electrodes when the processing circuitry determines there is a fault condition.

In one aspect of the embodiment, each of the plurality of electrodes includes a thermocouple, the thermocouple having a first wire and a second wire, each of the first and second wires being in communication with the CEDS. In one aspect of the embodiment, the fault condition is a connection fault condition, the processing circuitry being configured to determine whether there is a connection fault condition in at least one of the first and second wire. In one aspect of the embodiment, the connection fault condition is one of: at least one of the first and second wires is disconnected from the CEDS; and at least one of the first and second wires is intermittently connected to the CEDS.

In one aspect of the embodiment, the CEDS further includes a first pullup resistor connected to the first wire and a second pullup resistor connected to the second wire, the first pullup resistor being driven at a first voltage and the second pullup resistor being driven at a second voltage, the first and second voltages being different. In one aspect of the embodiment, the processing circuitry is configured to determine whether there is a connection fault condition by: recording a thermocouple voltage from each thermocouple; comparing the recorded thermocouple voltage from each thermocouple to a first threshold voltage; and determining that that there is a connection fault condition in only a first wire of a thermocouple from which a recorded thermocouple voltage is greater than the first threshold voltage.

In one aspect of the embodiment, the first wire is a positive wire and the second wire is a negative wire.

In one aspect of the embodiment, the recorded thermocouple voltage is the difference between a wire voltage recorded for the first wire and a wire voltage recorded for the second wire.

In one aspect of the embodiment, the processing circuitry is further configured to determine whether there is a connection fault condition by: comparing the recorded thermocouple voltage from each thermocouple to a second threshold voltage; and determining that there is a connection fault condition in both a first wire and a second wire of a thermocouple from which a recorded thermocouple voltage is greater than the second threshold voltage.

In one aspect of the embodiment, the processing circuitry is further configured to determine whether there is a connection fault condition by: comparing the recorded thermocouple voltage from each thermocouple to a third threshold voltage; and determining that there is a connection fault condition in only a second wire of a thermocouple from which a recorded thermocouple voltage is less than the third threshold voltage.

In one aspect of the embodiment the energy generator further includes an integrating current monitor having a short integration time and a high-energy delivery circuit having a first half bridge and a second half bridge, the fault condition being an excessive charge delivery, the processing circuitry being configured to determine whether there is an excessive charge delivery by: monitoring a current passing through the first half bridge and the second half bridge; integrating the current in real time during the delivery of treatment energy; determining an integral value of the current; and determining the fault condition exists if the integral value is a value other than zero.

In one aspect of the embodiment, the fault condition is a location fault condition, the processing circuitry being configured to determine whether there is a location fault condition by: recording a temperature from each thermocouple; comparing the recorded temperature from each thermocouple from the recorded temperature from each of the other thermocouples and determining if the recorded temperatures compared to each other are different by more than a first threshold difference; comparing the recorded temperature from each thermocouple to at least one of a first temperature threshold range and a second temperature threshold range, and determining if the compared recorded temperature for at least one thermocouple is outside the at least one of the first temperature threshold range and the second temperature threshold range; and determining that there is a location fault condition when: the recorded temperatures are different by more than the threshold difference; and the compared recorded temperature for at least one thermocouple is outside the at least one of the first temperature threshold range and the second temperature threshold range. In one aspect of the embodiment, the threshold difference is approximately 1° C., the first temperature threshold range is between approximately 36° C. and approximately 39° C., and the second temperature threshold range is greater than approximately 8° C. above an ambient temperature.

In one aspect of the embodiment, the energy generator further includes a plurality of energy delivery transistors, the processing circuitry being configured to automatically terminate a delivery of treatment energy by reverse biasing all of the plurality of energy delivery transistors.

In one aspect of the embodiment, the energy generator further includes a plurality of supplemental transistors and a high-energy delivery circuit, the processing circuitry being further configured to automatically terminate a delivery of high voltage energy to the high-energy delivery circuit by reverse biasing all of the plurality of supplemental transistors.

In one aspect of the embodiment, the energy generator further includes a high-energy delivery circuit, the at least one relay of the energy generator being an at least one vacuum relay configured to interrupt energy delivery from the high-energy delivery circuit. In one aspect of the embodiment, the at least one relay of the catheter electrode distribution system (CEDS) is an at least one vacuum relay configured to interrupt energy delivery from the high-energy delivery circuit.

In one embodiment, a method of delivering treatment energy from a medical system, the medical system including a device having a plurality of electrodes, an energy generator, and a catheter electrode distribution system (CEDS), the method including: performing a plurality of pre-checks, the plurality of pre-checks including: recording a temperature measurement from each of the plurality of electrodes and determining a pre-check fault condition exists if at least one of: the recorded temperature measurements differ from each other by more than a threshold amount; and at least one of the recorded temperature measurements is less than a threshold temperature; recording an impedance measurement from each of the plurality of electrodes and determining a pre-check fault condition exists if at least one of: at least one of the recorded impedance measurements is outside a threshold impedance range; and a bipolar impedance between adjacent electrodes of the plurality of electrodes is outside a threshold bipolar impedance range; measuring a current passing through a monitor within the energy generator within each of a long integration period and a short integration period, calculating an integrated current, and determining a pre-check fault condition exists if the integrated current (charge) is greater than a threshold integrated current (charge) amount; and determining whether at least one of a first electrode wire and a second electrode wire are disconnected from the CEDS and determining a pre-check fault condition exists when at least one of the first electrode wire and the second electrode wire are disconnected from the CEDS; and initiating a delivery of treatment energy from the energy generator when no fault conditions are determined to exist.

In one aspect of the embodiment, the method further includes: after the initiation of the delivery of treatment energy, determining whether at least one of the first electrode wire and the second electrode wire are disconnected from the CEDS and determining a delivery fault condition exists when at least one of the first electrode wire and the second electrode wire are disconnected from the CEDS; and initiating at least one of an electronic safeguard and an electromechanical safeguard when the delivery fault condition is determined to exist.

In one aspect of the embodiment, the electronic safeguard includes at least one of a primary electronic safeguard and a redundant electronic safeguard and the electromechanical safeguard includes at least one of a primary electromechanical safeguard and a redundant electromechanical safeguard.

In one aspect of the embodiment, the primary electronic safeguard includes terminating the delivery of treatment energy from the energy generator by turning off a plurality of delivery transistors in the energy generator; the redundant electronic safeguard includes terminating the delivery of treatment energy from the energy generator by turning off a plurality of supplemental transistors in the energy generator; the primary electromechanical safeguard includes interrupting the delivery of treatment energy from the energy generator by activating at least one relay in the energy generator; and the redundant electromechanical safeguard includes interrupting the delivery of treatment energy from the energy generator by activating at least one relay in the CEDS.

In one aspect of the embodiment, the method may further include: after the initiation of the delivery of treatment energy, measuring a current passing through a monitor within the energy generator within each of a long integration period and a short integration period, measuring the current including measuring at least one instantaneous current during each of the long integration period and the short integration period and a peak current during each of the long integration period and the short integration period; establishing an in-treatment threshold current amount; and determining a fault condition exists if at least one of the measured at least one instantaneous current and peak current is one of greater than the in-treatment threshold current amount and less than the in-treatment threshold current amount.

In one embodiment, a medical system may include: a medical device including a treatment element having a plurality of electrodes, each of the plurality of electrodes having a thermocouple with a first thermocouple wire and a second thermocouple wire; an energy generator in communication with the plurality of electrodes, the energy generator including: processing circuitry being configured to determine if there is a connection fault in the at least one of the first and second thermocouple wires and to automatically terminate a delivery of treatment energy when the processing circuitry determines there is a fault condition; and at least one relay configured to selectively interrupt the communication between the energy generator and the plurality of electrodes when the processing circuitry determines there is a fault condition; and a catheter electrode distribution system (CEDS) in communication with the energy generator and the plurality of electrodes, each of the first and second thermocouple wires being in communication with the CEDS, the CEDS including: at least one relay configured to selectively interrupt the communication between the energy generator and the plurality of electrodes when the processing circuitry determines there is a fault condition; and a first pullup resistor connected to the first wire and a second pullup resistor connected to the second wire, the first pullup resistor being driven at a first voltage and the second pullup resistor being driven at a second voltage, the first and second voltages being different. The processing circuitry may be further configured to: record a thermocouple voltage from each thermocouple; compare the recorded thermocouple voltage from each thermocouple to each of a first threshold voltage, a second threshold voltage, and a third threshold voltage; and determine that there is a connection fault condition in only the first thermocouple wire of a thermocouple from which a recorded thermocouple voltage is greater than the first threshold voltage; determine that there is a connection fault condition in both the first and the second thermocouple wire of a thermocouple from which a recorded thermocouple voltage is greater than the second threshold voltage; and determine that there is a connection fault condition in only the second thermocouple wire of a thermocouple from which a recorded thermocouple voltage is less than the third threshold voltage.

In one embodiment, a method of delivering treatment energy from a medical system, the medical system including a device having a plurality of electrodes, an energy generator, a catheter electrode distribution system (CEDS), and at least one thermocouple, may include: determining a baseline temperature; delivering treatment energy through each of the plurality of electrodes; recording a post-treatment temperature measurement from each thermocouple; comparing the post-treatment temperature measurement to the pre-treatment measurement for each thermocouple to calculate a temperature difference determining a fault condition exists if the temperature difference for at least one thermocouple is greater than a threshold amount; and preventing a further delivery of treatment energy through each of the plurality of electrodes if the fault condition is determined to exist.

In one aspect of the embodiment, the baseline temperature may be selected from the group consisting of: a pre-treatment temperature measurement from the at least one thermocouple, the at least one thermocouple being associated with at least one of the plurality of electrodes; an ambient room temperature measurement; and a pre-treatment temperature measurement from the at least one thermocouple, the at least one thermocouple being located proximate an energy delivery path.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
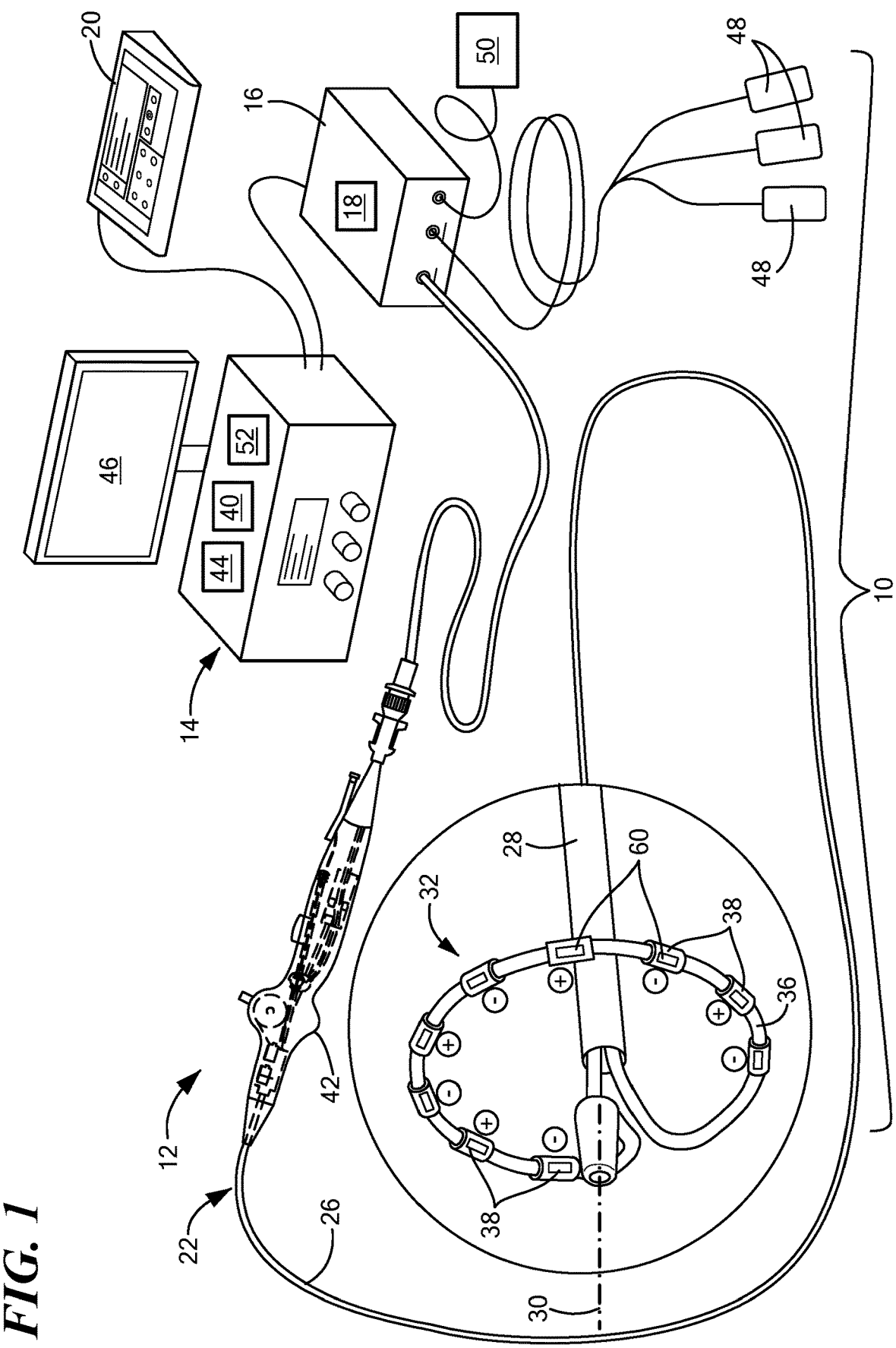
FIG. 1 shows an exemplary medical system for delivering treatment energy.

The systems and methods disclosed herein enhance the safety of delivery of treatment energy to a patient. For example, the systems and methods may include verification of system integrity before, during, or after the delivery of treatment energy and provides several mechanisms for rapid termination of the delivery of potentially harmful energy to the patient when a fault condition in the device and/or system is identified. The system may include an energy generator having processing circuitry to determine if there is a fault condition in the system and to automatically terminate a delivery of treatment energy when the processing circuitry determines there is a fault condition. The method may generally include performing a series of pre-checks, synchronizing a treatment energy delivery to the proper segment of the heart's depolarization pattern, configuring the system for treatment energy delivery, delivering the treatment energy, monitoring during energy delivery, and performing post-treatment evaluation.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawing figures in which like reference designations refer to like elements, an embodiment of a medical system constructed in accordance with the principles of the present invention is shown in FIG. 1, generally designated as "10." The system 10 may generally include a medical device 12 that may be coupled directly to an energy supply, such as a pulsed electric field or radiofrequency (RF) generator 14 including an energy control, delivering, and monitoring system or indirectly through a catheter electrode distribution system 16 (CEDS). The CEDS 16 may include an impedance meter 18 for testing the integrity of the energy delivery pathway, as discussed in more detail below. The system 10 may also include a remote controller 20 that is in communication with the generator 14 for operating and controlling the various functions of the generator 14. Further, the medical device 12 may include one or more diagnostic or treatment regions for the energetic, therapeutic, and/or investigatory interaction between the medical device 12 and a treatment site. As a non-limiting example, the treatment region(s) may deliver pulsed field electroporation energy and/or radiofrequency energy to a tissue area in proximity to the treatment region(s).

The medical device 12 may be a treatment and mapping device. The medical device 16 may include an elongate body 22 passable through a patient's vasculature and/or proximate to a tissue region for diagnosis or treatment. For example, the device 12 may be a catheter that is deliverable to the tissue region via a sheath or intravascular introducer (not shown). The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28.

The medical device 12 may further include one or more treatment elements 34 at, coupled to, or on the elongate body distal portion 28 for energetic, therapeutic, and/or investigatory interaction between the medical device 12 and a treatment site or region. As a non-limiting example, the device 12 may include a treatment element 34, such as that shown in FIG. 1, that includes a carrier element 36 bearing a plurality of electrodes 38. The carrier element 36 may be transitionable between a linear configuration and an expanded configuration in which the carrier element 36 has an arcuate or substantially circular configuration. Alternatively, the medical device 12 may have a substantially linear configuration with the plurality of electrodes 38 located in a common longitudinal axis along the length of at least a portion of the elongate body distal portion 28 (for example, a focal catheter). However, it will be understood that the treatment element may have any configuration and number of electrodes or treatment elements that is suitable for a particular procedure.

The plurality of electrodes 38 may also perform diagnostic functions, such as collection of intracardiac electrograms (EGM) and/or monophasic action potentials (MAPs) as well as performing selective pacing of intracardiac sites for diagnostic purposes. Measured signals may be transferred from the catheter electrode energy distribution system 16 to a recording system input box 40, which may be included in or integrated with the generator 14. The plurality of electrodes 38 may also monitor the proximity to target tissues and quality of contact with such tissues using impedance based measurements with connections to the catheter electrode energy distribution system 16. The catheter electrode energy distribution system 16 may include high speed relays to disconnect/reconnected specific electrodes 38 from the generator 14 during an energy delivery procedure. Immediately following the pulsed energy deliveries, the relays may reconnect the electrode(s) 38 so they may be used for diagnostic purposes.

Although not shown, the system 10 may include one or more sensors to monitor the operating parameters throughout the system, in addition to monitoring, recording or otherwise conveying measurements or conditions within the medical device 12 or the ambient environment at the distal portion of the medical device 12. The sensor(s) may be in communication with the generator 14 and/or the electrode distribution system 16 for initiating or triggering one or more alerts or therapeutic delivery modifications during operation of the medical device 12.

The medical device 12 may include a handle 42 coupled to the elongate body proximal portion 26. The handle 42 may include circuitry for identification and/or use in controlling of the medical device 12 or another component of the system. Additionally, the handle 42 may also include connectors that mate to the generator 14 and/or the electrode distribution system 16 to establish communication between the medical device 12 the generator 14 and/or the electrode distribution system 16. The handle 42 may also include one or more actuation or control features that allow a user to control, deflect, steer, or otherwise manipulate a distal portion of the medical device 12 from the proximal portion of the medical device 12.

The generator 14 may include processing circuitry 44, including a processor and a memory, in communication with one or more controllers and/or memories containing software modules containing instructions or algorithms to provide for the automated operation and performance of the features, sequences, calculations, or procedures described herein and/or required for a given medical procedure. As a non-limiting example, the memory may be in electrical communication with the processor and have instructions that, when executed by the processor, configure the processor to monitor the system 10 for a fault condition, establish one or more safety thresholds as discussed herein, and initiate one or more of the safeguards discussed herein. Further, the generator 14 may include one or more displays 46 for displaying information about the system, patient, procedure, or the like to the user and optionally for receiving input or commands from the user. The system 10 may further include a plurality of surface ECG electrodes 48 in communication with the generator 14 through the catheter electrode distribution box 16. When the surface electrodes 48 are applied to the skin of a patient, they may be used, for example, to monitor the patient's cardiac activity to determine pulse train delivery timing at the desired portion of the cardiac cycle and/or for navigation and location of the device 12 within the patient. In addition to monitoring, recording, or otherwise conveying measurements or conditions within the medical device 12 or the ambient environment at the distal portion 28 of the medical device 12, additional measurements may be made through connections to the multi-electrode device, such as temperature, electrode-tissue interface impedance, delivered charge, current, power, voltage, work, or the like in the generator 14 and/or the device 12. The surface ECG electrodes 48 may be in communication with the generator 14 for initiating or triggering one or more alerts or therapeutic deliveries during operation of the medical device 12. Additional neutral electrode patient ground patches 50 may be used to evaluate the desired electrical path impedance, as well as monitor and alert the operator upon detection of undesired and/or unsafe conditions.

Figure 2:
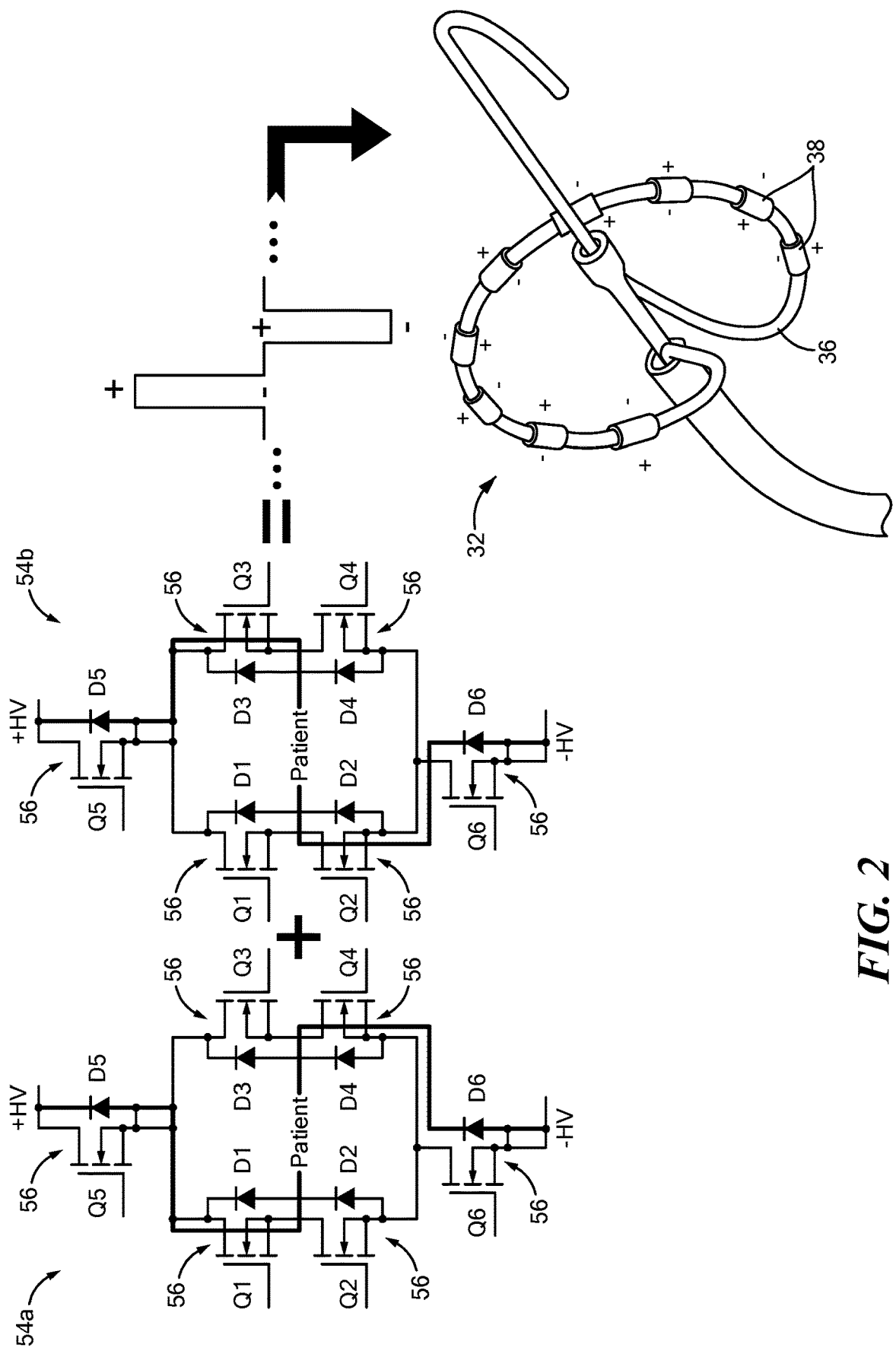
FIG. 2 shows a circuit diagram for a currently known waveform function generator and delivery of biphasic energy to a treatment element of a medical device.

Referring now to FIG. 2, a circuit diagram for a currently known waveform function generator is shown. The PFA energy generator 14 may provide electrical pulses to the medical device 12 to perform an electroporation procedure to cardiac tissue or other tissues within the patient's body, such as renal tissue, airway tissue, and organs or tissue within the cardiac space. Specifically, generator 14 may be configured and programmed to deliver pulsed, high-voltage electric fields appropriate for achieving desired pulsed, high-voltage ablation (referred to herein as "pulsed field ablation" or "pulsed electric field ablation") and/or pulsed radiofrequency ablation. For example, the generator 14 may include a waveform function generator component 52 that provides the keying current to a high-voltage "H bridge" 54 (as shown in FIG. 2), which, in turn, generates the high-amplitude biphasic waveform. The "H bridge" may also be referred to herein as a "high-energy delivery circuit 54." This biphasic waveform is output to the device electrodes 38. Normal H bridge 54 operation occurs when field effect transistors (FETs) or insulated gate bipolar transistors (IGBTs) 56 (referred to herein collectively as "energy delivery transistors 56" or "transistors 56") Q1/Q4 and Q2/Q3 alternately conduct to create a biphasic pulse between device electrodes 38 within the patient. These two alternative states are shown in FIG. 2 as 54*a* and 54*b*.

The system shown in FIG. 2 is simple and effective for researching the effects of PFA in animals, but it leaves a human patient extremely vulnerable to electrocution hazards. Noting that the patient is connected to the H bridge output, there are six transistors 56 that must be fully functioning in order to isolate the patient from the high voltage power supply. During the "off" state when treatment energy is not delivered to the patient, transistors Q1-Q6 are reverse biased and present impedance on the order of gigohms (1e9 Ohms) to prevent DC current from flowing to a patient.

A severe electrocution hazard exists if transistors Q1 and Q4 (or Q2 and Q3) develop a leakage resistance on the order of 150 M ohm (1.5e6 Ohms or less), causing a leakage current of 10 microamps (1e-5 or greater) to flow through patient connections. If this leakage condition were to occur, then a direct current (DC) will flow through a patient and present an electrocution risk. Therefore, the leakage must be detected, the delivery of treatment energy terminated, and patient connections removed immediately. With proper closed-loop control, it is possible to detect a leak and disconnect the patient within a few microseconds. Given a current of 40 amps, this limits delivered charge to less than 100 microcoulombs (1e-4 Coulombs), or, for example, an amount similar to a pacing pulse applied via an implantable pacemaker. This corrective action may then render what would have been a life-threatening hazard into a harmless event.

Figure 6:
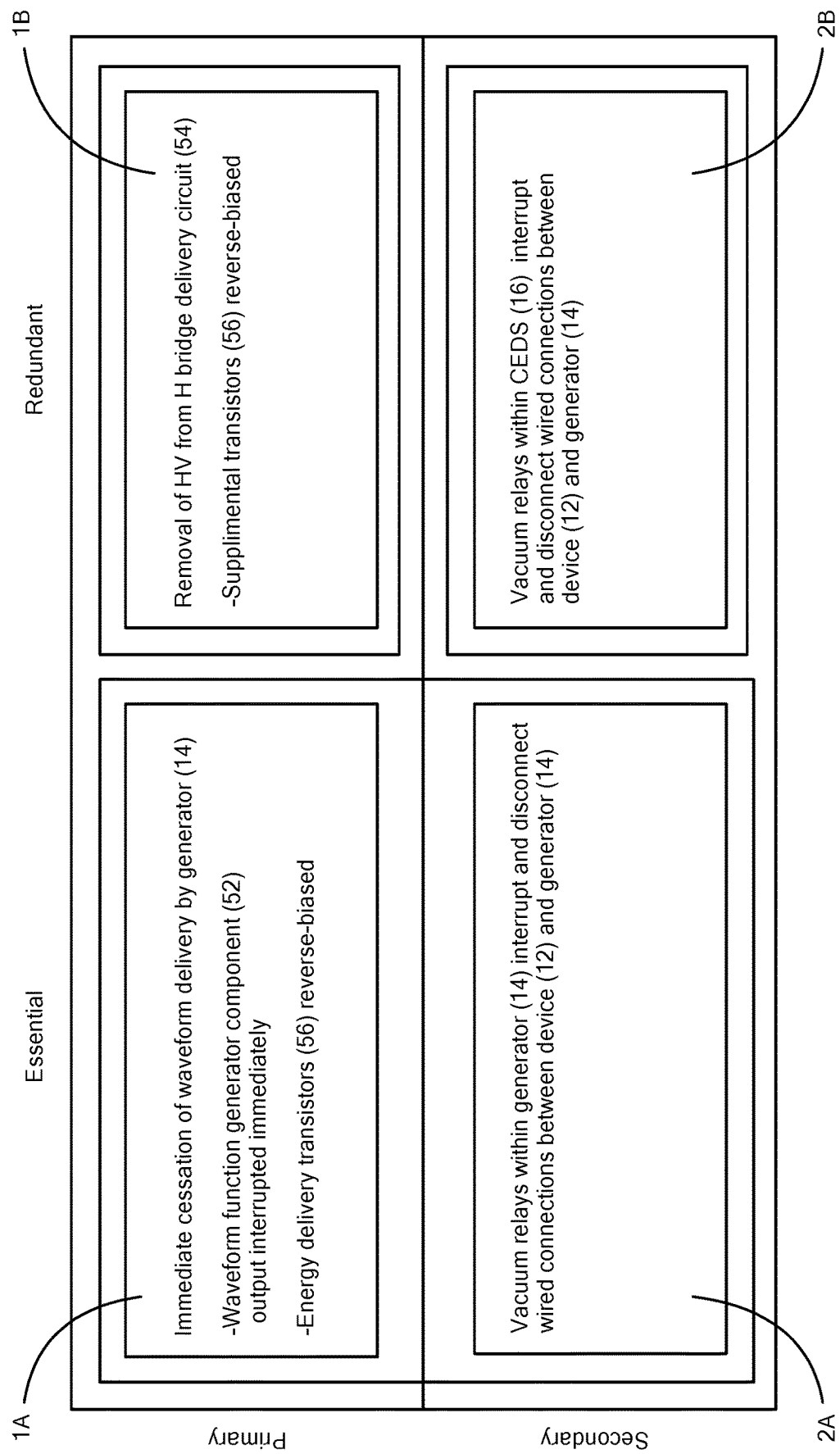
FIG. 6 shows a chart illustrating the relationship between primary and secondary electronic and electromechanical protection mechanisms.

Therefore, the system 10 may be configured to monitor fault indications of irregular energy delivery to the patient as well as monitor errant operation of the generator 14. These protection mechanisms may include purely solid-state electronic safeguards, which may provide a way of immediately terminating inadvertent energy delivery to the patient, and electromechanical safeguards controlled by relays that may react more slowly, but that can remove physical wired connections to the patient. Further, the protection mechanisms may include essential and redundant safeguards (as shown in FIG. 6)

Figure 3A:
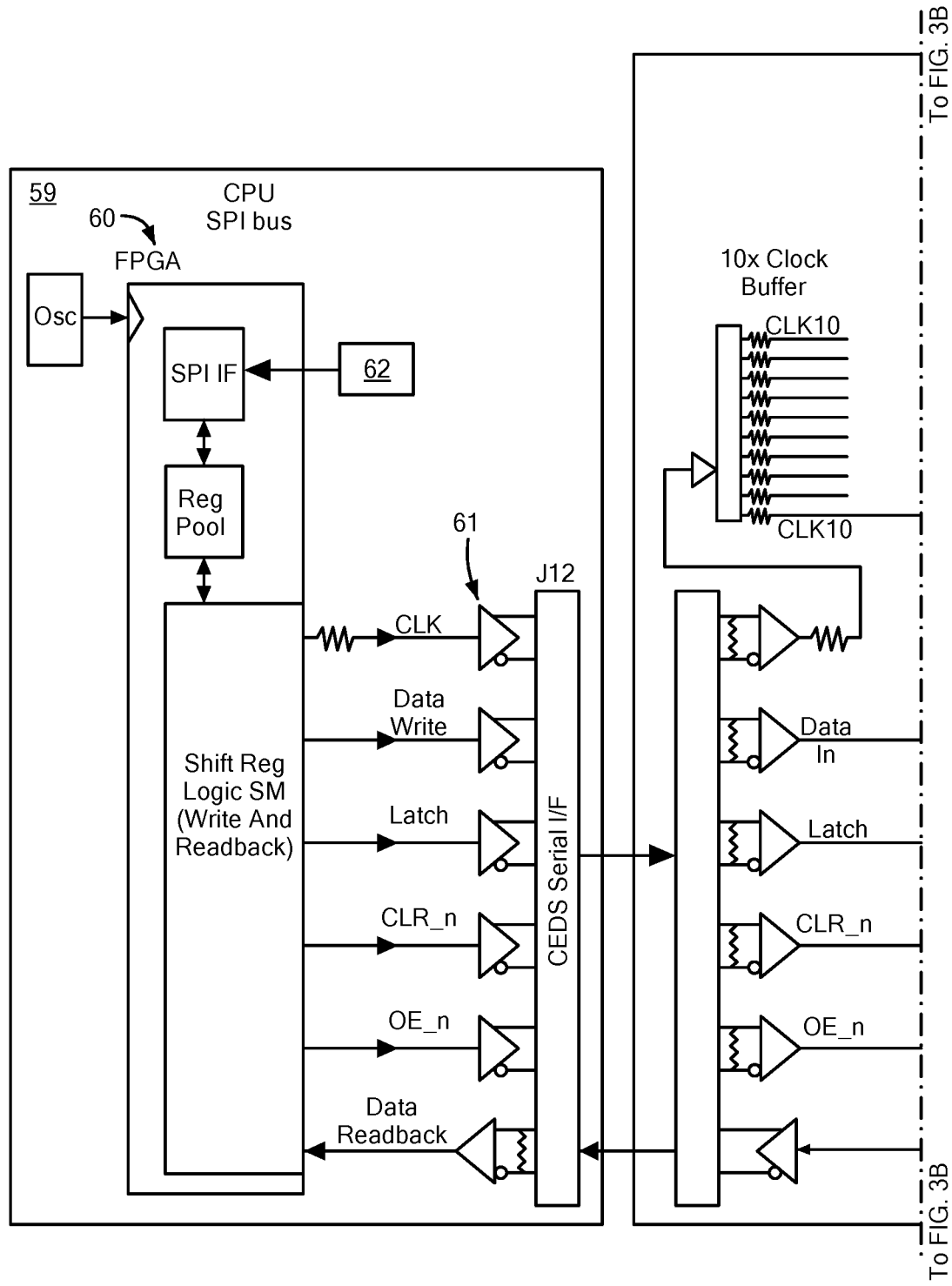
FIGS. 3A and 3B show a serial interface circuit diagram between a temperature sensing board and a catheter electrode distribution system.
Figure 3B:
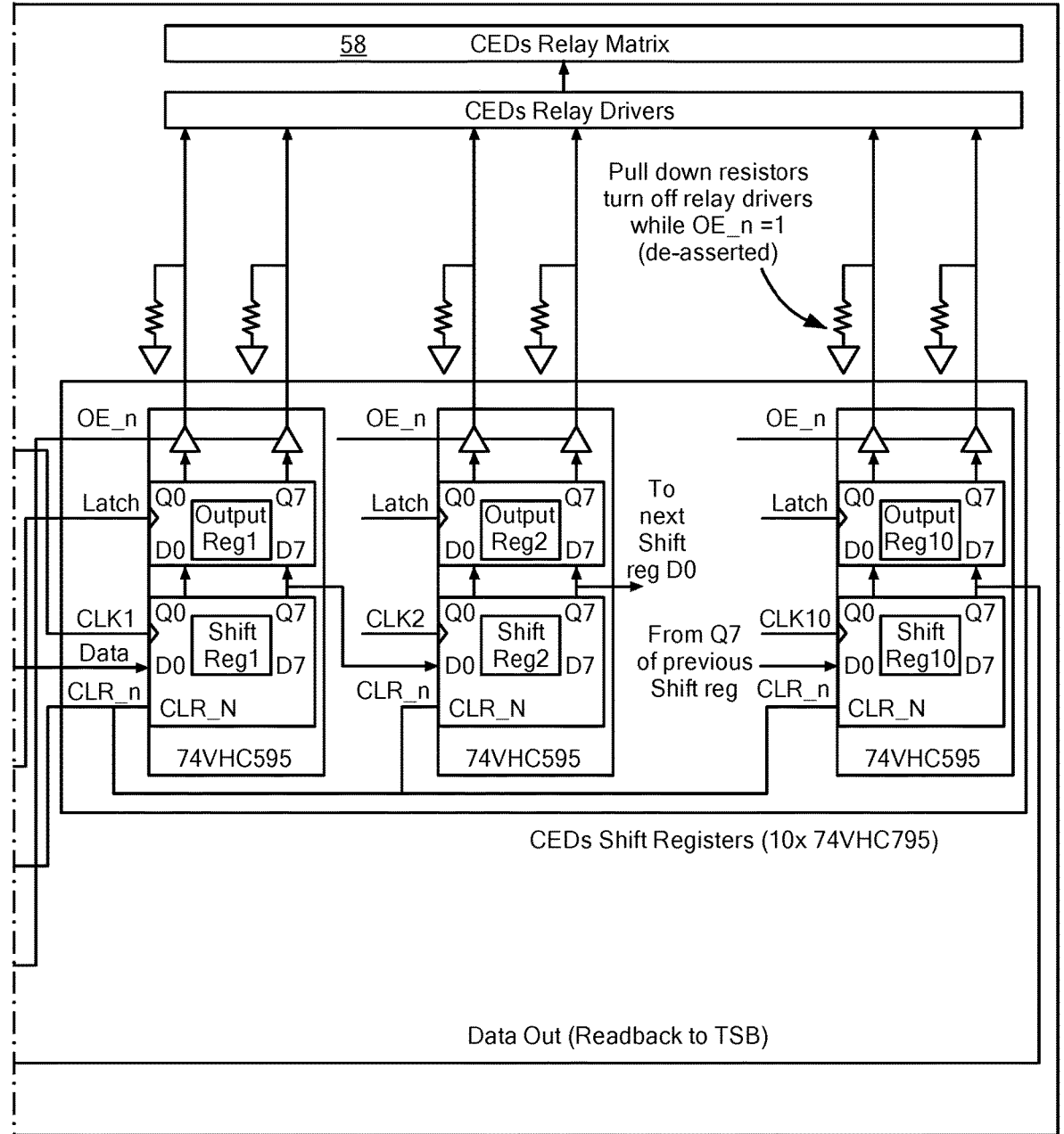

To enact the electronic safeguards, the generator processing circuitry 44 may include processing circuitry with dedicated logic and analog circuits to automatically terminate the delivery of treatment energy. Additionally, to enact the electromechanical safeguards, the generator 14 and CEDS 16 may each include a secondary mechanism including a set of normally open, high-power (both high-voltage and high-current) relays 58 (which may also be referred to herein as a relay matrix) used to physically remove circuit connections to the patient. For example, the generator delivery relays 58a and CEDS delivery relays 58b are circled by a dashed line in FIG. 15 for illustration. The reaction time of the main electronic protection mechanisms may be on the order of a few microseconds, whereas the secondary electromechanical relay response times may be a bit longer, on the order of less than 10 milliseconds. The electronic safeguards may be the primary protection mechanisms and the electromechanical safeguards may be the secondary protection mechanisms. The electronic and electromechanical safeguards are redundant in that there may be two means of electronic safeguards, namely, waveform cessation and high voltage removal, and two locations of relays for the electromechanical safeguards, namely, within the generator 14 (relays 58a) and the CEDS 16 (relays 58b). This relationship is shown in the chart of FIGS. 3A and 3B.

The system 10 may also include a temperature sensing board 59 (TSB) that, in conjunction with the CEDS 16, is used to control the relay matrix 58. As a non-limiting example, the TSB 59 and the CEDS 16 may be housed in the same housing component or otherwise in communication and associated with each other. Prior to enabling the relays 58 (such as through the common output enable (OE) signal), the system may perform a register readback to ensure that the relay matrix 58 will be properly configured. The TSB 59 may generally include a field-programmable gate array 60 (FPGA) and at least one low-voltage differential signaling (LVDS) driver 61. An interface between the FPGA 60 of the TSB 59 and the CEDS 16 is shown in FIGS. 3A and 3B. Additionally, the FPGA 60 may include an interface between CEDS processing circuitry 62, located on the TSB 59, and serial peripheral interface (SPI) bus (indicated as "SPI IF" in FIG. 3A), a register pool (indicated as "Reg Pool" in FIG. 3A), and a shift register logic (indicated as "Shift Reg Logic SM (Write and Readback)" in FIG. 3A). This interface within the FPGA 60 may involve six signals: CLK, Data In (Write), Latch, Clear, Output Enable, and Data Out (Readback), each being associated with an LVDS driver 61 using differential signaling (with $Z_0$ equal to 100 hms). A description of these signals is shown in the Table 1 below. In Table 1, the term "rising edge" and "falling edge" refer to those points in a digital signal where it changes from 0 to 1 or from 1 to 0, respectively. The edges of an electrical clock signal are used to synchronize other actions in a circuit. For example, data output may change on the falling edge of the clock and the data input records data on the rising edge of the clock. Further, an active low signal, or logical "0," engages the "clear," whereas a logical "1" prevents the "clear."

TABLE 1

Serial interface signal descriptions.

| Signal | Description |
| --- | --- |
| Shift Enable | FPGA internal signal. Rising edge of this signal instructs the TSB 59 to start shifting data to the CEDS 16. Generated by the CEDS processing circuitry 62 into the FPGA 60, via the SPI interface/register pool. |
| CLK | Serial data clock. Generated by the shift register logic/state machine. |
| Data In | Serial data out from the TSB 59 into the CEDS 16. Synchronized with the CLK falling edge. CEDS 16 shifts this data on the next CLK rising edge. |
| Data In Finished | FPGA internal pulse to indicate that all serial data was shifted out of the TSB 59 into the CEDS 16. |
| Latch | Rising edge transfers data from the shift register stage to the output register stage on the CEDS 16. |
| CLR_n | Asynchronous clear of the shift register stage on the CEDS 16 (active low signal). Asserting this signal clears the shift register stage, but not the output register stage on the CEDS 16. A Latch rising edge is issued next to clear the output register stage content. |
| Data Out | Serial data out from the CEDS 16 back into the TSB 59. Synchronized with the CLK rising edge. The TSB 59 shifts this data in on the next CLK falling edge. |
| Data Readback Finished | FPGA internal pulse to indicate that all serial data was shifted out of the CEDS 16 into the TSB 59. |
| OE_n | Output Enable (active low signal) on the output register stage of the CEDS 16. When de-asserted (high signal, or logical "1"), the CEDS relay drivers 58 are forced to the default state ("off" state wherein all relays are open) via the CEDS onboard pulldown resistors. |
| Data Match | FPGA internal pulse indicating that serial data readback = serial data written. |
| Data Mismatch | FPGA internal pulse indicating that serial data readback ≠ serial data written. |

Figure 4:
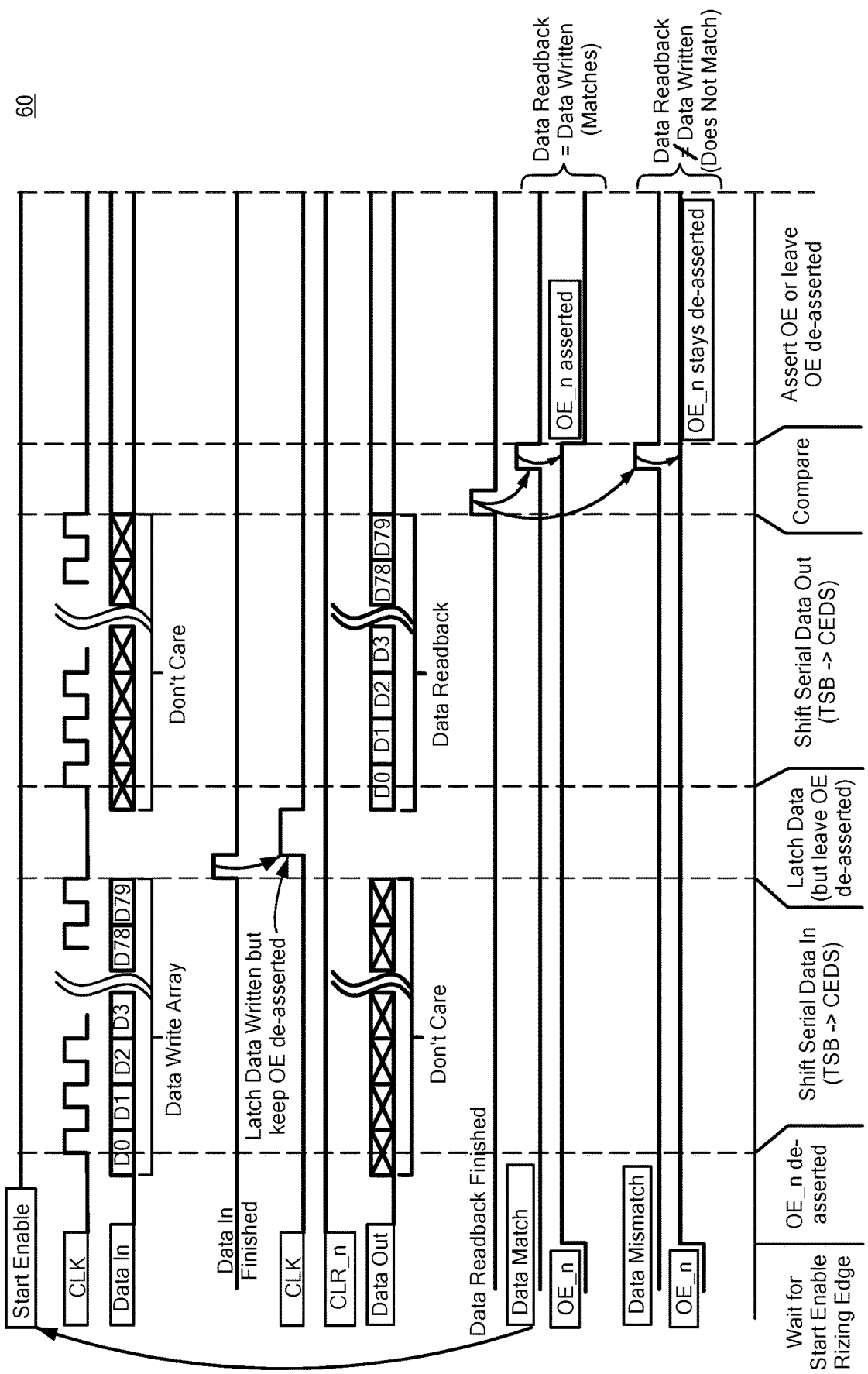
FIG. 4 shows exemplary timing for a method of operation of the serial interface circuit shown in FIGS. 3A and 3B.
Figure 5:
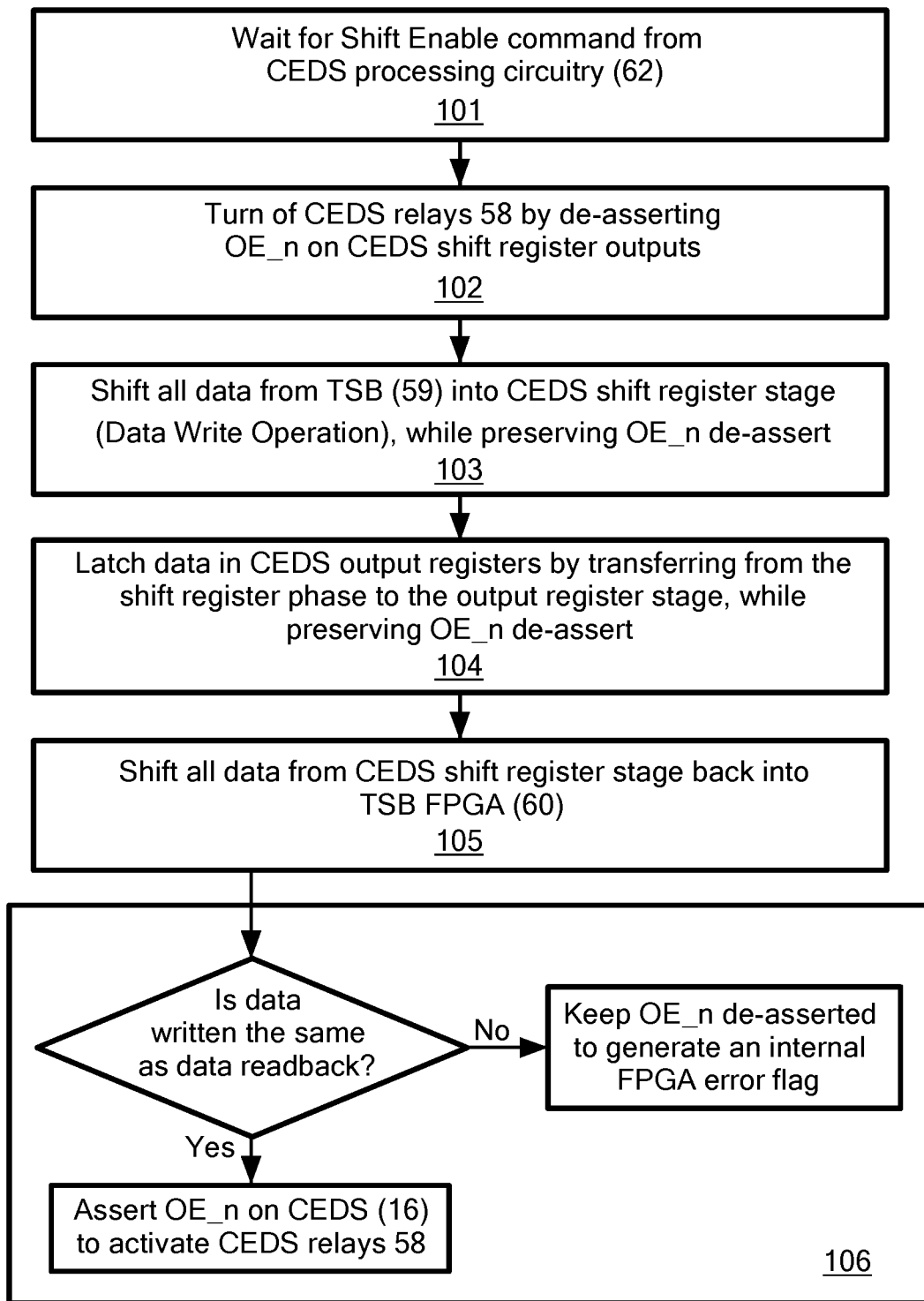
FIG. 5 shows a flow chart for the method of operation of the serial interface circuit of FIGS. 3A and 3B.

During operation, the shift register logic of the TSB 59 may follow the method shown in FIG. 5. Further, the method may involve the timing steps shown in FIG. 4. In the first step 101, the shift register logic may wait for the Shift Enable command from the CEDS processing circuitry 62. In the second step 102, the CEDS relays 58 may be turned off by de-asserting OE_n (logic "1") on the CEDS shift register outputs (force in tri-state). In order to turn off the CEDS relays 58, the input to the CEDS relay drivers are active high inputs and have pulldown resistors to force them into the off state. Additionally, in the exemplary schemes shown in FIGS. 3A-4, the CEDS 16 may contain 10×8 bit registers (or small units of memory). In the third step 103, all data may be shifted from the TSB 59 into the CEDS 16 shift register stage (Data Write operation), while preserving the OE_n de-assert. In the fourth step 104, data may be transferred from the shift register stage (shift registers are indicated as "Shift Reg1," "Shift Reg2," etc. in FIG. 3B) to the output register stage (output registers are indicated as "Output Reg1," "Output Reg2," etc. in FIG. 3B) on the CEDS 16 (Latch), while preserving the OE_n de-assert. In the fifth step 105, data may be shifted from the CEDS shift register stage back into the TSB FPGA 59 (Data Readback operation). The output registers hold a shift register's data and allow it to remember its output data even while the data is being shifted back to the FPGA 59 for readback. The output enable is shown in FIG. 3B by the small triangles (buffers) with OE_n signals leading into them. The output buffers allow output to be disabled until it can be confirmed that the data was read correctly. In the sixth step 106, the CEDS processing circuitry 62 may compare if the data written is the same as the data readback. If so, the CEDS relays 58 may be activated or turned on by asserting OE_n (logic "0") on the CEDS 16. If the data written is not the same as the data readback, the CEDS relays 58 may continue to be de-asserted and the TSB 59 may generate an internal FPGA "error flag" to indicate data readback mismatch to the CEDS processing circuitry 62. Thus, a data readback mismatch may cause the system 10 to prevent activation of the relay matrix 58 and, therefore, prevent the delivery of energy to the patient by the generator 14.

Referring again to the electronic safeguards, the two primary electronic safeguards in response to a fault may be: (1) immediate cessation of waveform delivery by the generator 14, wherein the waveform function generator component's 52 output is interrupted immediately and all energy delivery transistors 56 are turned off (reverse biased), shown in Box 1A of FIG. 6; and (2) removal of high voltage (HV) from the H bridge delivery circuit 54, shown in Box 1B of FIG. 6. In addition to the four energy delivery transistors 56 in the H bridge 54, there are two additional transistors 56 that may serve as switches to apply or remove HV to the H bridge 54 (which may be referred to as "supplemental transistors"). For example, these supplemental transistors 56 are transistors Q5 and Q6 in FIG. 2. For safeguard (1), transistors 56 (Q1-Q4) are turned off (reverse biased). For safeguard (2), these two supplemental transistors 56 (Q5 and Q6) may be immediately turned off (reverse biased) and voltage removed from the H bridge 54 in the case of a fault.

Additionally, the two secondary electromechanical safeguards may be: (1) high-power vacuum relays that are in line with each of the bipolar bridge outputs, as shown in Box 2A in FIG. 6; and (2) interruption of patient physical connections from the generator 14, as shown in Box 2B in FIG. 6. As for safeguard (1), the vacuum relays may interrupt and disconnect the wired connections between the device 12 within the patient and the generator 14. The vacuum relays may be under the direct control of fault detection logic in the generator 14. As for safeguard (2), the CEDS 16 may use the same type of high-voltage, high-current vacuum relays to connect or disconnect bridge connections to the device electrodes 38. As such, these relays may be able to interrupt patient physical connections from the generator 14, but at a location closer to the patient. These generator delivery relays 58a and CEDS delivery relays 58b are encircled by dashed lines in FIG. 15 for illustration.

Figure 7:
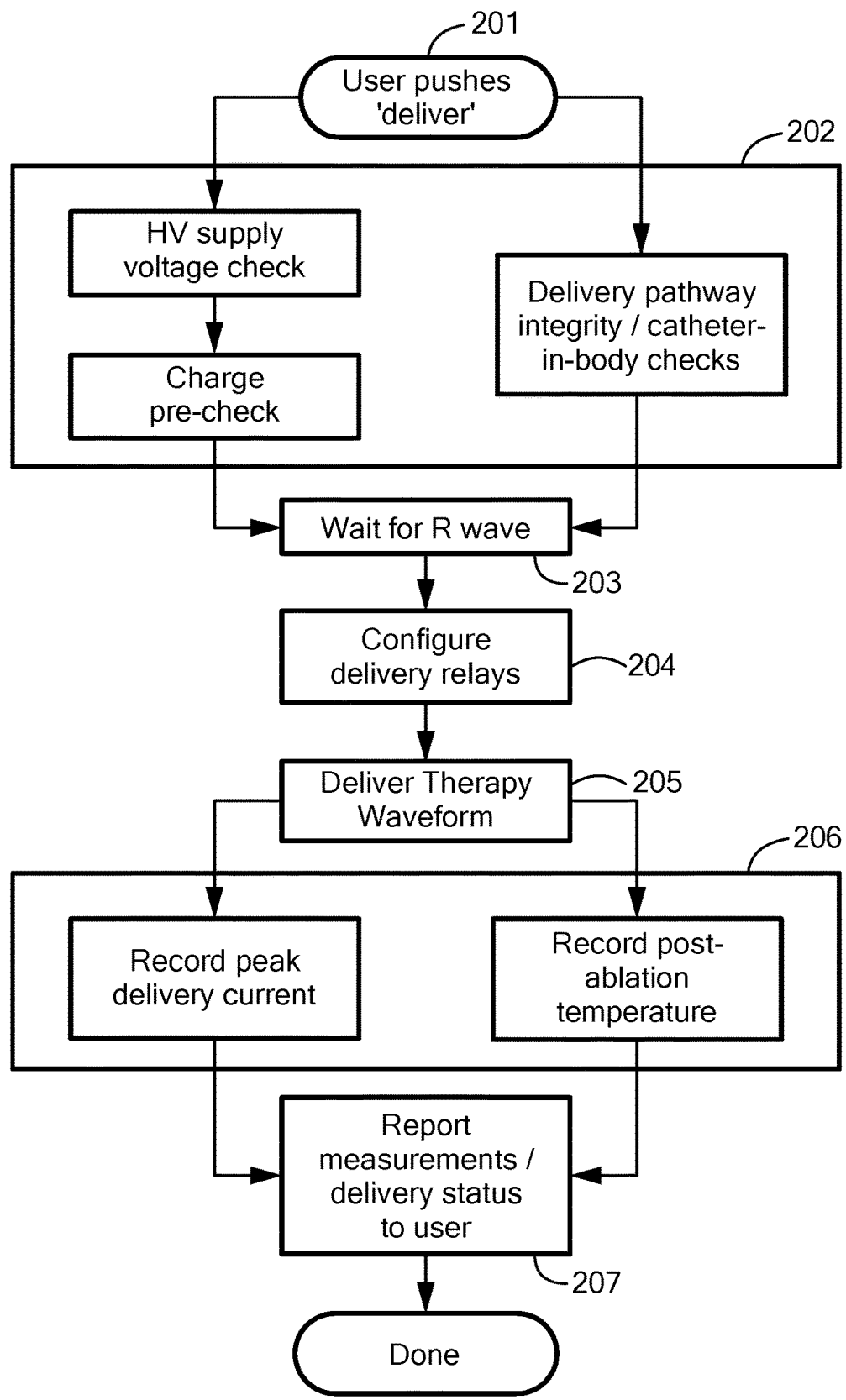
FIG. 7 shows a method of treatment energy delivery with steps for ensuring patient safety.

Referring now to FIG. 7, a method of safely delivering treatment energy is shown. In general, the method may include performing a series of pre-checks, synchronizing a treatment energy delivery to the proper segment of the heart's depolarization pattern, configuring the system for treatment energy delivery, delivering the treatment energy, and performing post-treatment evaluation. Additionally, any of the pre-check and post-evaluation methods may be performed continuously or at varying times before, during, and after the treatment energy delivery (in other words, the pre-check methods may be performed before the treatment energy delivery, but may also be performed during or after delivery). Normal depolarization of the right and left ventricles is represented on an electrocardiogram by a series of waves and deflections, including a QRS complex followed by a T wave (not shown). The S and T portion may be referred to as the "ST segment." Treatment energy, such as PFA energy, is delivered during the heart's ST segment to avoid the risk of inducing cardiac arrhythmia. In addition to applying the voltage waveform, there are other steps required for the safe delivery of treatment energy. Thus, the system 10 provides for efficient sequencing and synchronization of delivery mechanisms.

In the first step 201, the user may activate the generator 14 to deliver treatment energy (voltage waveform). However, before energy is actually delivered to the device 12, several safety pre-checks may first be executed in the second step 202. For example, the generator 14 and/or CEDS 16 may be configured to execute an HV supply voltage check, a charge pre-check, and one or more pathway integrity checks. In order to minimize time between R-wave synchronization and the delivery of treatment energy, the safety pre-checks may be performed after the user activates the generator 14 in the first step 201, but before the R-wave synchronization. Additionally or alternatively, although the flow chart of FIG. 7 shows this activation as the first step 201, some or all of the safety pre-checks of the second step 202 may be performed before activation of the generator 14 for delivery, such as when the generator 14 is in an "armed" or "standby" mode. This way, the safety pre-checks can be completed before the generator 14 is initiated for delivery, which may reduce time between initiation and delivery.

As a non-limiting example, the one or more pathway integrity checks may include a catheter integrity check and a catheter in-body check. The in-body checks may include two mechanisms to determine device location and ensure that treatment energy delivery does not occur outside the patient's body. The first mechanism may involve temperature measurement. The device 12 may include one or more thermocouples 63 or temperature sensors in the treatment element 34 or elsewhere. Based on temperature measurements received by the generator 14 from the thermocouples 63, the generator 14 may prevent delivery of treatment energy. For example, each thermocouple 63 may measure a temperature at the electrode/tissue interface. If temperatures measured by two or more thermocouples 63 differ by more than a threshold amount, for example, by greater than 2° C., the generator 14 may prevent the delivery of treatment energy to the device 12. Likewise, the generator 14 may prevent the delivery of treatment energy to the device 12 if an absolute temperature measured by one or more thermocouples 63 is less than a threshold temperature, for example, 35° C., or is greater than a threshold temperature, for example, 40° C., or if one or more thermocouples 63 measures a rate of temperature change that is greater than a threshold rate. The second mechanism may involve impedance measurement. Impedance may be measured at each electrode 38 and the generator 14 may prevent the delivery of treatment energy to the device 12 is the measured impedance at a frequency between 4 khz and 100 khz from any electrode to patient ground is outside a predetermined impedance value range of, for example, 50-500 Ohms, and/or if the bipolar impedance between any adjacent electrodes is outside a predetermined impedance value range of, for example, 40-300 Ohms difference in bipolar impedance between different pairs. In addition to the safety features utilizing temperature measurements to prevent energy deliveries, such measurements may be used to warn the user that excessive electrode heating was measured, halting subsequent deliveries until the user takes some action. Such a temperature rise may be detected in the period immediately following a delivery of a series of energy pulses. Algorithms may be enabled to prevent subsequent deliveries and alert the operator of this condition if a temperature rise of, for example, greater than 13° C. is detected immediately following an energy delivery.

For the voltage pre-check, the generator 14 may be configured to perform a voltage check by ensuring that the delivery voltage is within a predetermined percentage or predetermined voltage from a nominal set point. For example, when the user selects a treatment profile from the generator 14, the generator 14 may set its HV supply to a corresponding voltage. It may take several seconds for the generator to reach that voltage, so the generator 14 may continually monitor the HV supply voltage until the intended voltage is reached. Immediately before delivery, the generator 14 may perform a single measurement of the HV supply voltage to ensure it is still at the intended voltage. Any deviation from the intended voltage, except for a small tolerance window, may indicate a hardware or software fault.

Figure 8:
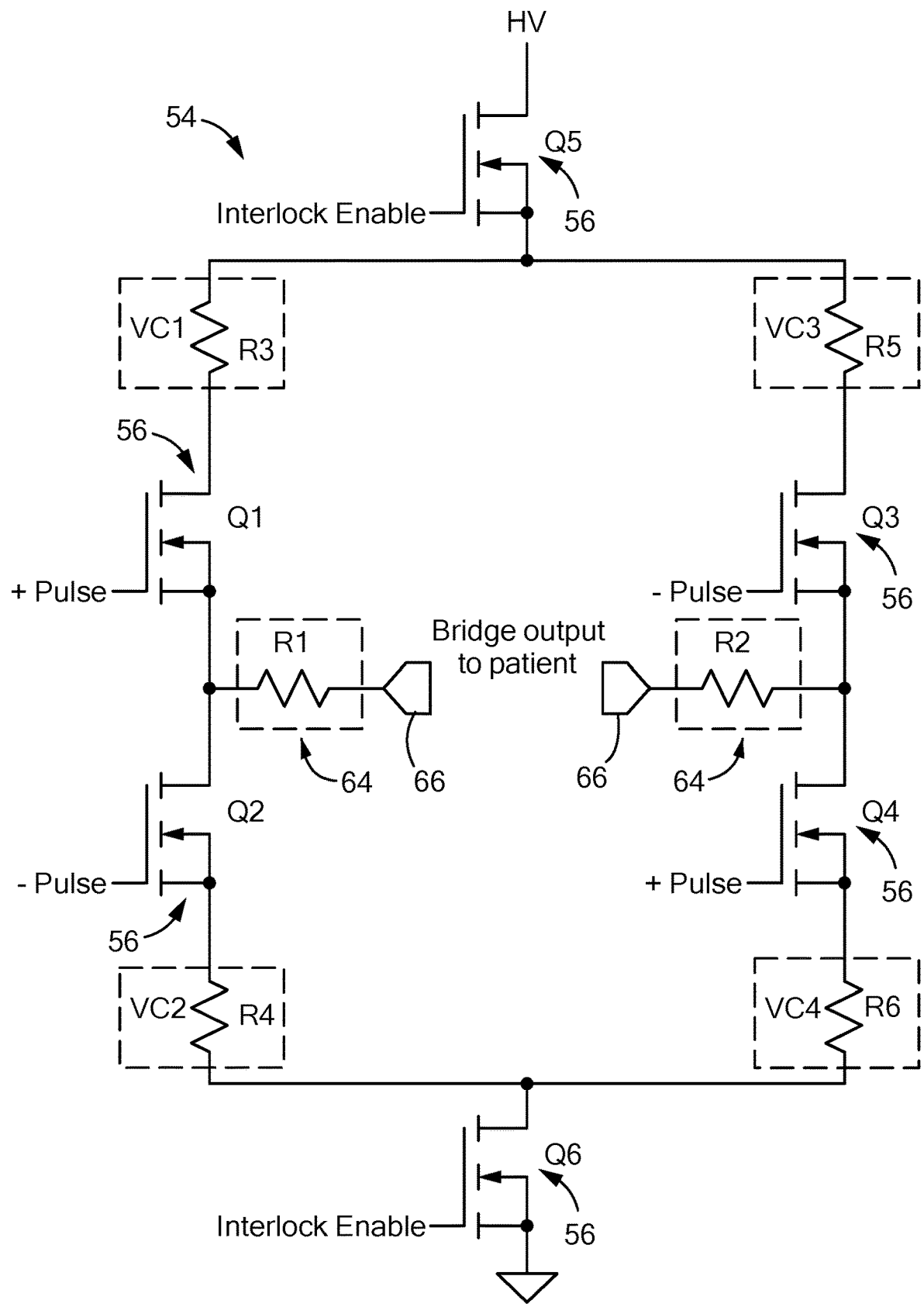
FIG. 8 shows a circuit diagram for an exemplary high energy delivery circuit.
Figure 22:
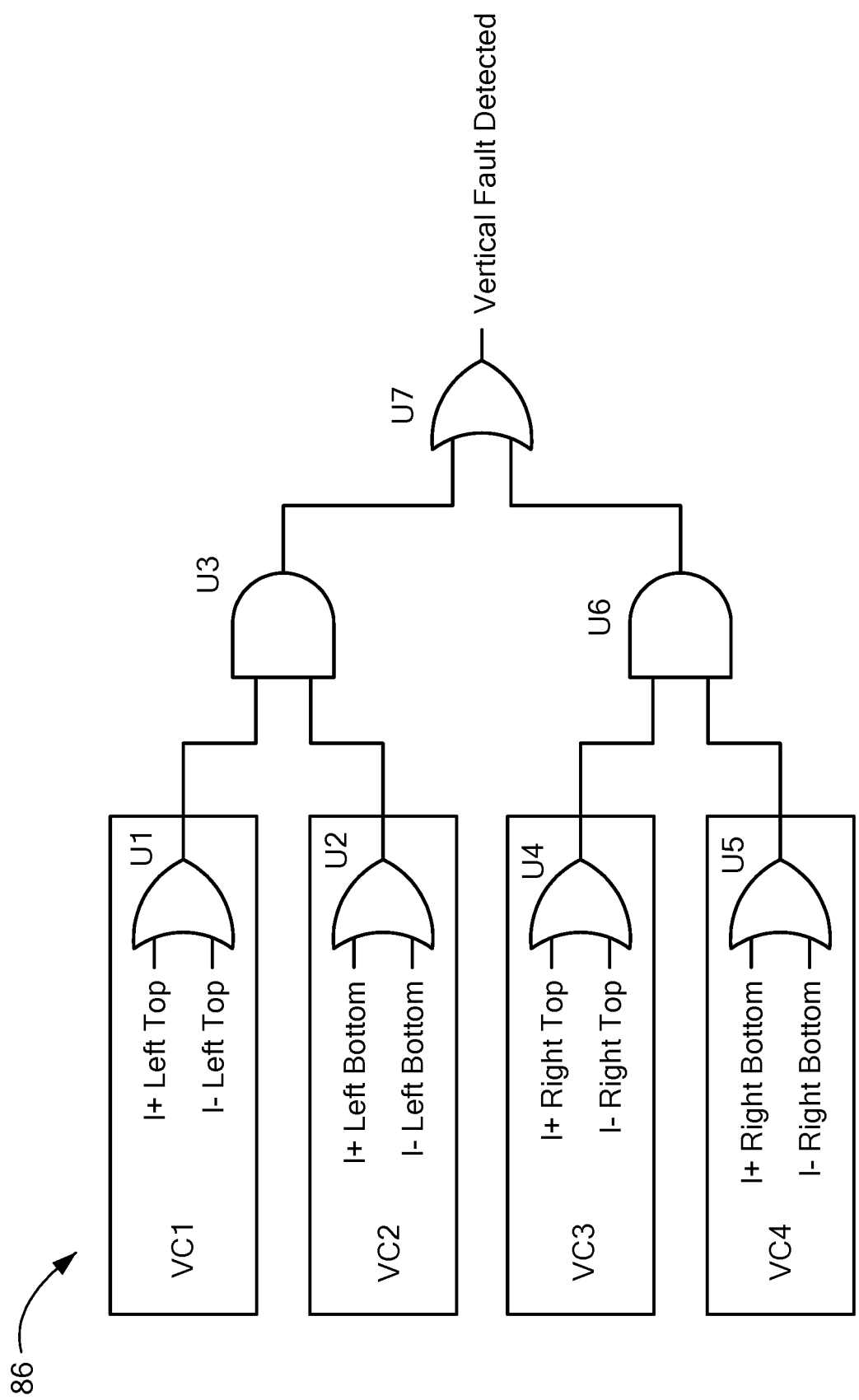
FIG. 22 shows a diagram of a vertical current fault logic.
Figure 23:
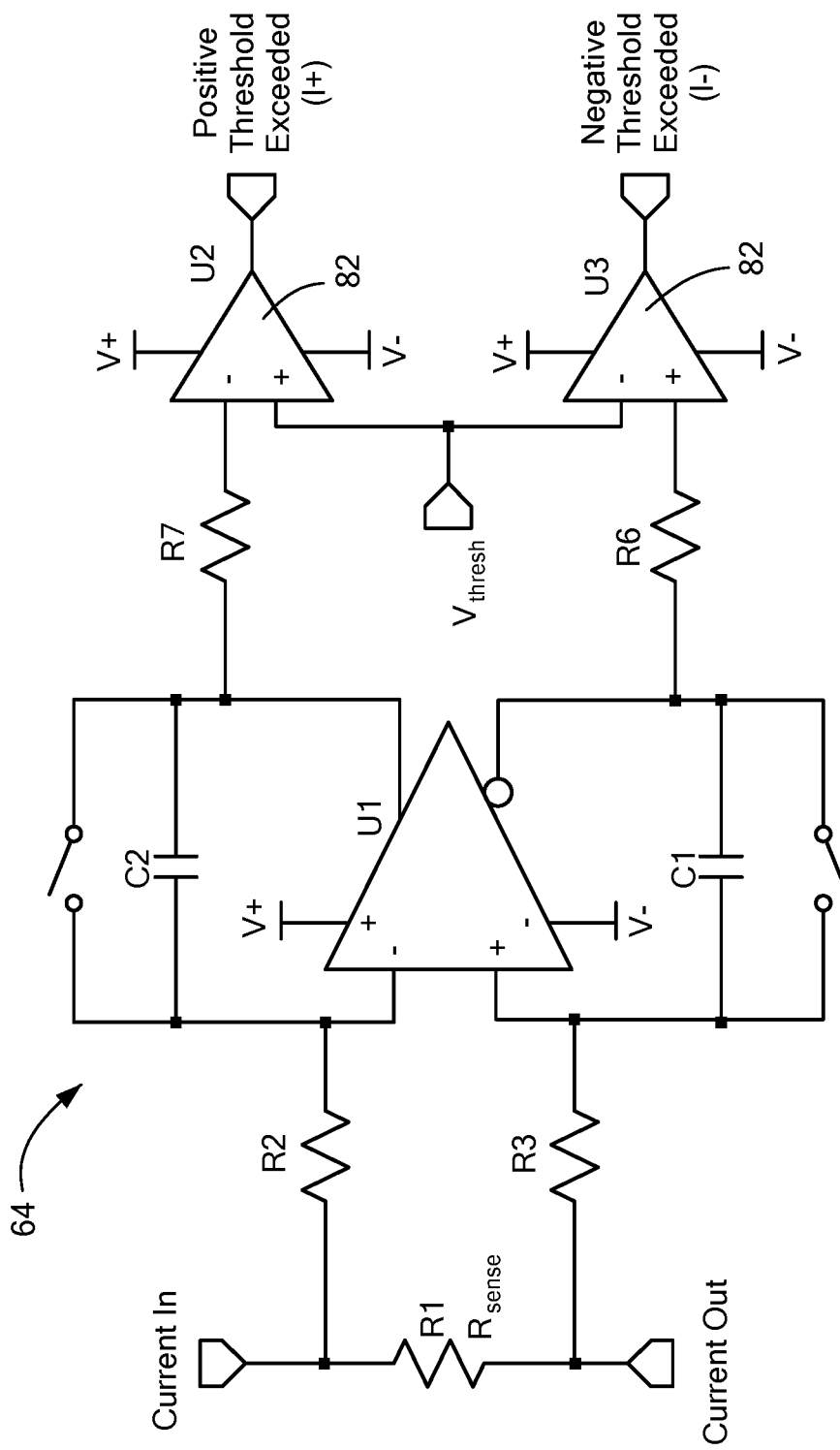
FIG. 23 shows a diagram of a charge monitor.

For the charge pre-check, the generator 14 may be configured to test for damage to the transistors 56 that are engaged prior to each treatment energy delivery, before the patient would be put at risk. One hazard of energy delivery, such as pulsed high voltage energy delivery, is that one or more transistors 56 in the output stage will partially short from drain to source, causing a small current leak. This can cause a DC voltage across the device 12, which poses a significant risk of causing cardiac arrhythmia. As a non-limiting example, the generator 14 may include a set of integrating current or charge monitors 64 located on the two outputs 66 of the delivery H bridge 54 (across resistors R1 and R2 as shown in FIG. 8). A more detailed diagram of each charge monitor 64 is shown in FIG. 22. Each H bridge output 66 may have two monitors 64 with long and short integration periods. The monitors with long integration periods may be used as part of the charge pre-check to identify small amounts of leakage before a patient connection is made. If too much net current passes through a monitor 64 within its integration period, it will signal a fault condition. Each delivery and safety transistor 56 can be individually tested for leakage before delivering treatment energy to the patient. To accomplish this, relays may attach a resistive dummy load to the H bridge output 66 in the place of the patient. Then, all transistors 56 in a delivery path are forward biased (either all of transistors Q6, Q1, Q4, Q5, or all of Q6, Q3, Q2, and Q5 as shown in FIG. 8) except the transistor 56 being tested. The single reverse-biased transistor 56 should prevent all current flow. If the transistor 56 does leak, the small current will cause the monitor to signal a fault condition. The fault threshold and test duration may be chosen in relation to expected physiologic response, anticipated noise sources, and agency-imposed limits. For example, the minimum amount of change needed to induce cardiac stimulation may be 50 nanocoulombs, and IEC 60601-1 patient auxiliary current limits may be 10 microamps. Thus, a limit may be set at 50 nC integrated over 5 microseconds. Any excursion above the set threshold may be considered a fault.

Figure 13:
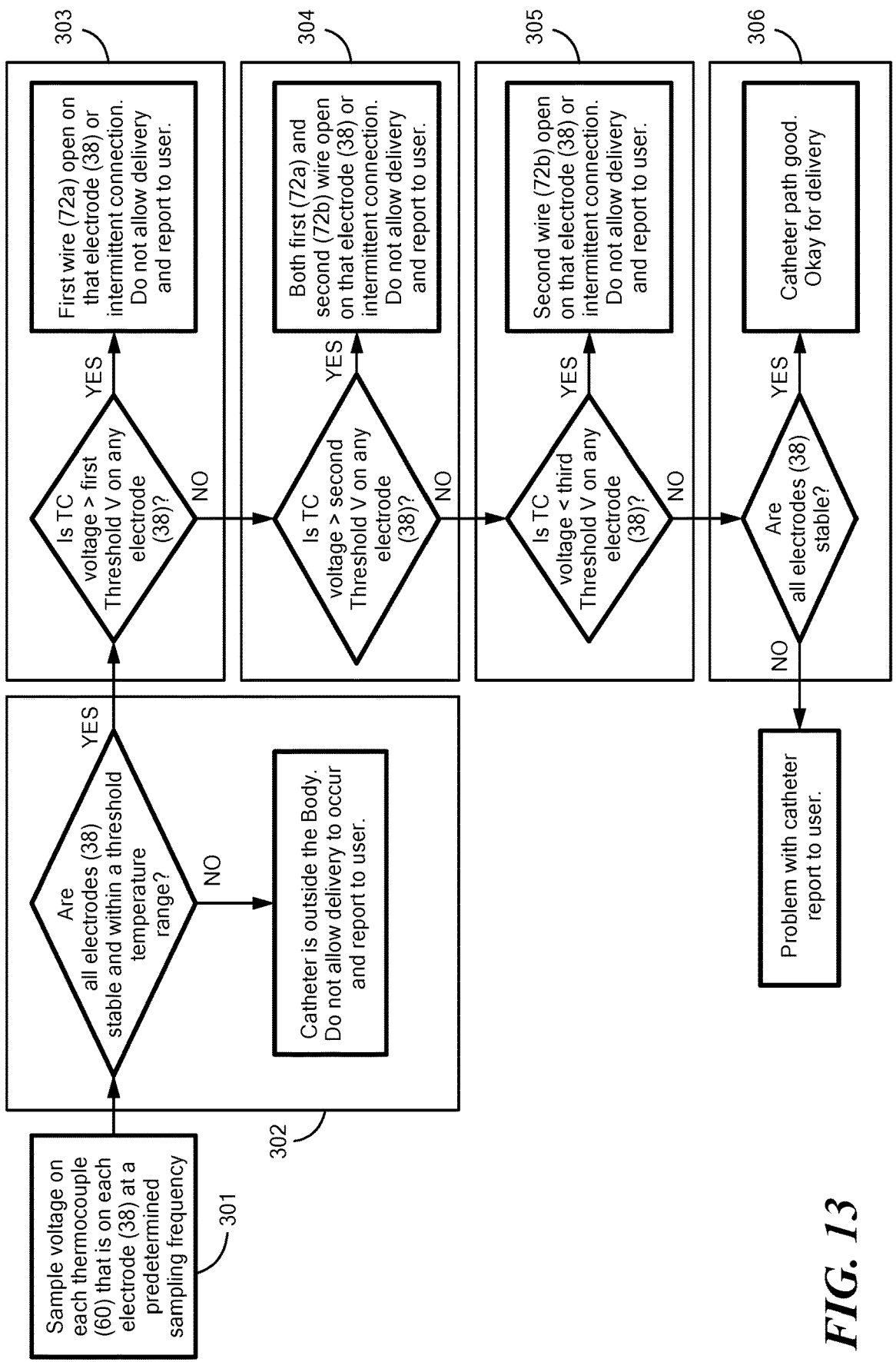
FIG. 13 shows an algorithm used to evaluate catheter integrity and to verify the device is within the patient.

Referring now to FIG. 13, an algorithm used during the pre-check process (in the second step 202 of the method shown in FIG. 7) to evaluate catheter integrity and to verify the device is within the patient is shown. In the first step 301, the processing circuitry 44 may sample the voltage on each thermocouple 63 that is on or associated with an electrode 38 at a predetermined sampling frequency. As a non-limiting example, the voltage may be sampled by delivering energy to each electrode 38 at a sampling frequency of at least approximately 8 Hz. However, it will be understood that the voltage may be sampled at any suitable frequency.

In the second step 302, at least one temperature measurement is recorded by each thermocouple 63. The processing circuitry 44 may then determine if the temperature measurements from the thermocouples 63 indicate that the thermocouples 63 of all electrodes 38 are stable (that is, within a predetermined temperature difference from each other) and within a threshold temperature range. As a non-limiting example, the processing circuitry 44 may determine that the electrodes 38 are stable if the associated thermocouples 63 record temperatures that are within approximately 2° C. of each other. Further, the threshold temperature range may be between approximately 36° C. and approximately 39° C. Alternatively, the threshold temperature range may include any temperature that is at least 8° C. above the room temperature. However, it will be understood that the threshold temperature range may be any range suitable for the device, procedure, and/or patient. If the thermocouples 63 of all electrodes 38 are stable and within the threshold temperature range, the processing circuitry 44 may determine that the device 12 is within the patient's body and move to the next step. If the conditions of the test of the second step 302 are not met, it may indicate that the device 12 is located outside of the patient's body and the processing circuitry 44 may prevent delivery of treatment energy to the device 12 and may alert the user, such as by the one or more displays 46 and/or other visual and/or audio alerts, of this condition. This condition may be referred to herein as a location fault condition.

In the third step 303, the processing circuitry 44 may determine whether the sampled voltage of any electrode thermocouple 63 from the first step 301 is greater than a first threshold voltage. The CEDS 16 may include a circuit including at least one pullup resistor 70 connected to each of a first thermocouple wire 72a and a second thermocouple wire 72b. The pullup resistors 70 are considered to be asymmetric in that the at least one pullup resistor 70a connected to the first thermocouple wire 72a is driven to a first voltage and the at least one pullup resistor 70b connected to the second thermocouple wire 72b is drive to a second voltage (shown in FIG. 14). The first threshold voltage may be based on the voltages used for the pullup resistors 70. As a non-limiting example shown in FIG. 14, each pullup resistor 70 may be a high-resistance pullup resistor 70 of approximately 10 M ohms, and the at least one pullup resistor 70*a* connected to the first wire 72*a* and the at least one pullup resistor 70*b* connected to the second wire 72*b* are driven to asymmetrical voltages of, for example, a first voltage, $V_p$, of +750 mV for a positive first thermocouple wire 72*a* (that is, a thermocouple wire connected to a positive terminal of a voltmeter 74 in the generator 14) and a second voltage, $V_n$, of +370 mV for a negative second thermocouple wire 72*b* (that is, a thermocouple wire coupled to a negative terminal of a voltmeter 74 in the generator 14). As a non-limiting example, the positive wire 72*a* may be composed of copper and the negative wire 72*b* may be composed of constantan. Further, the circuit shown in FIG. 14 may also include relays K1 and K2 that are closed by the system 10 in order to allow thermocouple voltage measurement.

Figure 14:
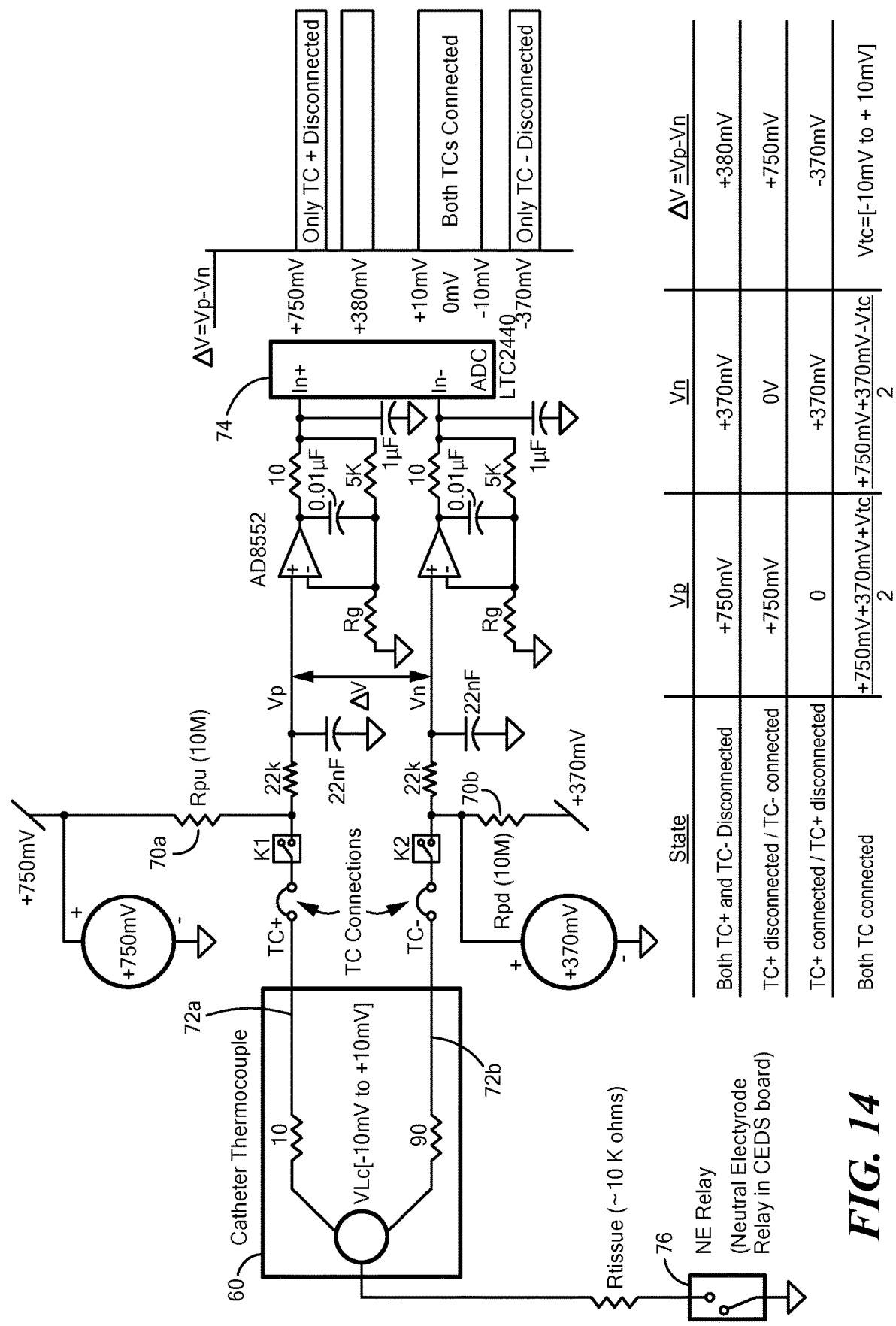
FIG. 14 shows a circuit diagram of a circuit used to evaluate thermocouple wire integrity.

As shown in FIG. 14, the difference in voltage, $\Delta V$, between the positive thermocouple wire 72*a* and the negative thermocouple wire 72*b* may be used for comparison to the threshold voltage. For example, if $V_p$ is +750 mV and $V_n$ is +370 mV and both wires 72*a*, 72*b* are disconnected, the $\Delta V$ is +38 mV. Likewise, if the negative wire 72*b* is connected (giving a measured voltage of 0 V), the $\Delta V$ is +750 mV. Finally, if the positive wire 72*a* is connected (giving a measured voltage of 0V), the $\Delta V$ is -370 mV. Comparing these values to the applicable threshold voltage may indicate the state of connection of the thermocouple wires 72. For example, if the negative wire 72*b* is connected (0 V) and the positive wire 72*a* is disconnected (+750 V from the pullup resistor 70), the $\Delta V$ of +750 mV is greater than a first threshold voltage of 600 mV.

Using the pullup resistor 70 characteristics described immediately above, the first threshold voltage may be 600 mV. If the voltage of a thermocouple 63 is greater than 600 mV, the processing circuitry 44 (and/or processing circuitry 63 within the CEDS 16) may determine that a thermocouple wire 72 is open (disconnected) and/or that there is an intermittent connection between the thermocouple wire 72 for that electrode 38 and the CEDS 16. Together these conditions may collectively be referred to as "connection fault condition" for simplicity. If the processing circuitry 44 determines that a sampled voltage from a thermocouple 63 is greater than 600 mV, the processing circuitry 44 may determine that the positive wire 72*a* of the associated electrode 38 is open or intermittently connected (that is, that there is a connection fault condition), and may prevent delivery of treatment energy to the device 12 and may alert the user of this condition. If the measured voltage is between approximately +10 mV and approximately -10 mV, the processing circuitry 44 may determine that both thermocouple wires 72 are connected (normal, operational condition).

If the sampled voltage from no thermocouple 63 is greater than the first threshold voltage (for example, 600 mV), the processing circuitry 44 may then determine whether the sampled voltage of any electrode thermocouple 63 is greater than a second threshold voltage in the fourth step 304. Like the first threshold voltage, the second threshold voltage may also be based on the voltage of the pullup resistors 70. As a non-limiting example using the pullup resistor characteristics described above, the second threshold voltage may be 150 mV. If a sampled voltage from a thermocouple 63 is greater than the second threshold voltage, the processing circuitry 44 may determine that both the positive thermocouple wire 72*a* and the negative thermocouple wire 72*b* are open for that electrode 38 (disconnected) and/or that there is an intermittent connection between the electrode wires 72*a*, 72*b* and the CEDS 16 (that is, that there is a connection fault condition). As a result, the processing circuitry 44 may prevent delivery of treatment energy to the device 12 and may alert the user of this condition.

If the sampled voltage from no thermocouple 63 is greater than the second threshold voltage (for example, 150 mV), the processing circuitry 44 may then determine whether the sampled voltage of any electrode thermocouple 63 is less than a third threshold voltage in the fifth step 305. Like the first and second threshold voltages, the third threshold voltage may be based on the voltage of the pullup resistors 70. As a non-limiting example, using the pullup resistor characteristics described above, the third threshold voltage may be -150 mV. If a sampled voltage from a thermocouple 63 is less than the third threshold voltage, the processing circuitry 44 may determine that the negative thermocouple wire 72*b* is open (disconnected) and/or that there is an intermittent connection between the electrode wire 72*b* and the CEDS 16 (that is, that there is a connection fault condition). As a result, the processing circuitry 44 may prevent the delivery of treatment energy to the device 12 and may alert the user of this condition.

If the sampled voltage from no thermocouple 63 is less than the third threshold voltage (for example, -150 mV), the processing circuitry 44 may then determine whether all electrodes 38 are stable (that is, within a predetermined temperature difference from each other) in the sixth step 306. As a non-limiting example, the predetermined temperature difference may be approximately 2° C. of each other. If the electrodes are determined to be stable, the device 12 is determined to be in good condition and the processing circuitry 44 will allow the delivery of treatment energy to the device 12. If the processing circuitry 44 determines that all electrodes 38 are not stable, the processing circuitry 44 may prevent the delivery of treatment energy to the device 12 and may alert the user of this condition.

Both temperature and voltage measurements may be taken continuously throughout the procedure in order to monitor device integrity using the algorithm as described above. It will be understood that the threshold voltages may be any suitable threshold voltages that allow for identification of a wire fault based on the asymmetrical voltages of the pullup resistor 70. Further, the pullup resistor 70 voltages may be chosen so they are within the analog-to-digital converter (ADC) conversion range of $\pm V_{ref}/2 = \pm 750$ mV, where $V_{ref}$ is +1500 mV. The CEDS may include a neutral electrode (NE) relay 76 that provides an electrical path to a neutral electrode patient ground patch 50. With the neutral electrode patient ground patch connected, the circuit may operate as descried. Without the neutral electrode patient ground patch connected, a fault in either or both wires may still be detected, as the voltage will rise above a threshold; however, identification of the wire in which the fault has occurred is not possible.

Before the system 10 is transitioned to the energy delivery mode, several relay checks may be performed. The system 10 is able to verify the electrical integrity of the entire energy delivery pathway from the device 12 to the H bridge 54 by using the impedance meter 18 located in the CEDS 16. The impedance meter 18 may be connected to the delivery pathway via a network of relays. By selectively closing the relays, the integrity of the entire delivery pathway can be verified in sections before connecting the patient to the generator's H bridge 54. Further, this integrity verification can be used by the processing circuitry 44 to determine whether one or more of the electrical and/or electromechanical safeguards discussed above should be enacted. Examples of relays used to verify portions of the delivery pathway are shown in FIGS. 12-16. Specifically, FIGS. 12-16 show the relay configurations required to conduct a test for verification that all relays close. However, it is also possible to conduct a test for verification that all relays open. To accomplish this, the processing circuitry 44 may instruct a relay being tested to open, but closes all other relays in a given test configuration. If the test is passed (that is, if the system resolves anything except an open circuit), then the system determines that the relay is stuck closed.

Figure 15:
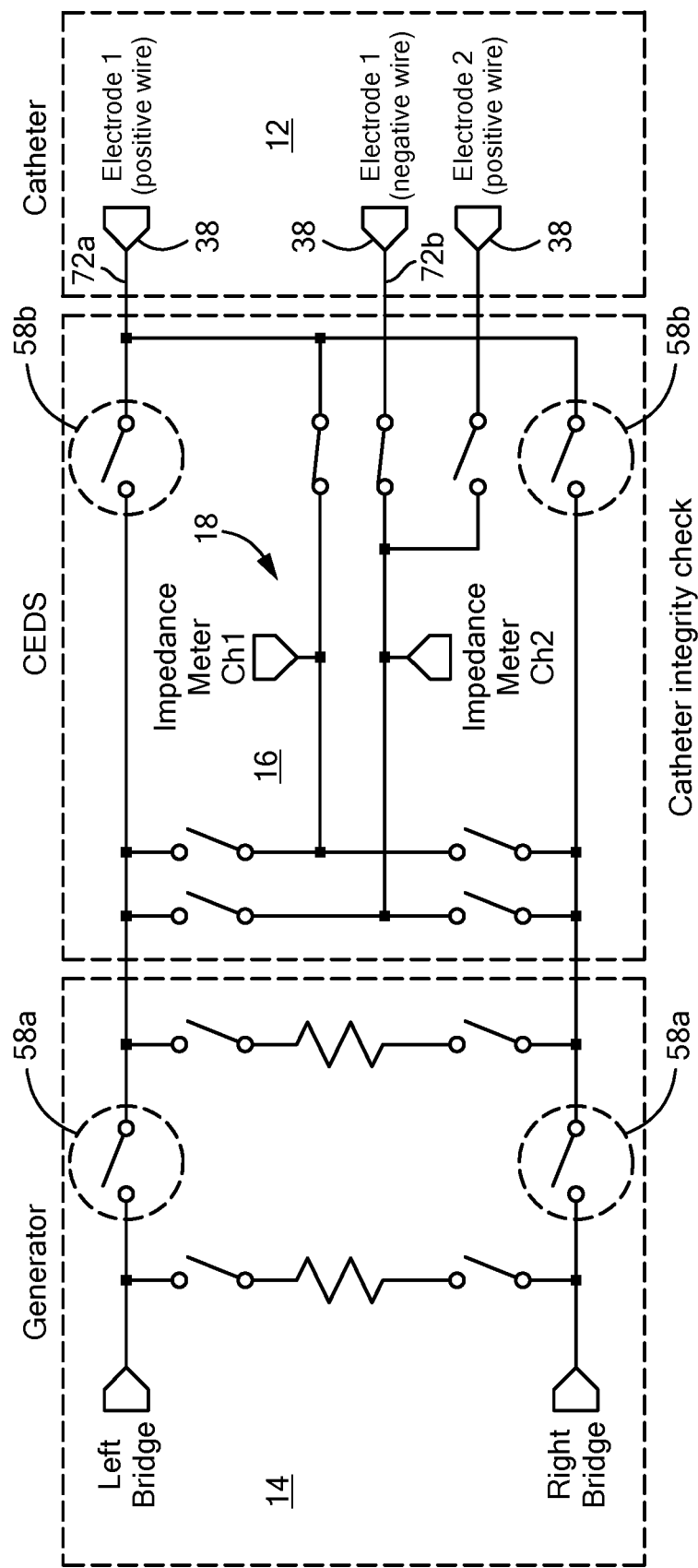
FIG. 15 shows a simplified diagram of relay configurations used to verify device integrity.

FIG. 15 shows a simplified diagram of relay configurations used to verify device integrity. It will be understood that some electrode connections in the generator 14 and CEDS 16 are omitted in FIGS. 12-16 for simplicity. For example, the CEDS 16 includes four connections for each electrode 38 (an electrode's positive wire 72a connects to the left bridge of the high energy delivery circuit 54, the right bridge of the high energy delivery circuit 54, and to one half of the impedance meter 18, and the electrode's negative wire 72b connects to the other half of the impedance meter 18). The device integrity test may use a pair of conductors 72a, 72b that both go to the same electrode 38. These conductors are typically used as the two thermocouple wires 72, but by measuring the impedance along their path, the system can verify the condition of the device 12. For example, an impedance measured by the impedance meter 18 that is less than expected may indicate a short circuit, whereas an impedance that is greater than expected may indicate an open circuit. Electrical impedance is measured between two points, shown as Ch1 and Ch 2 in FIGS. 12-16.

Figure 16:
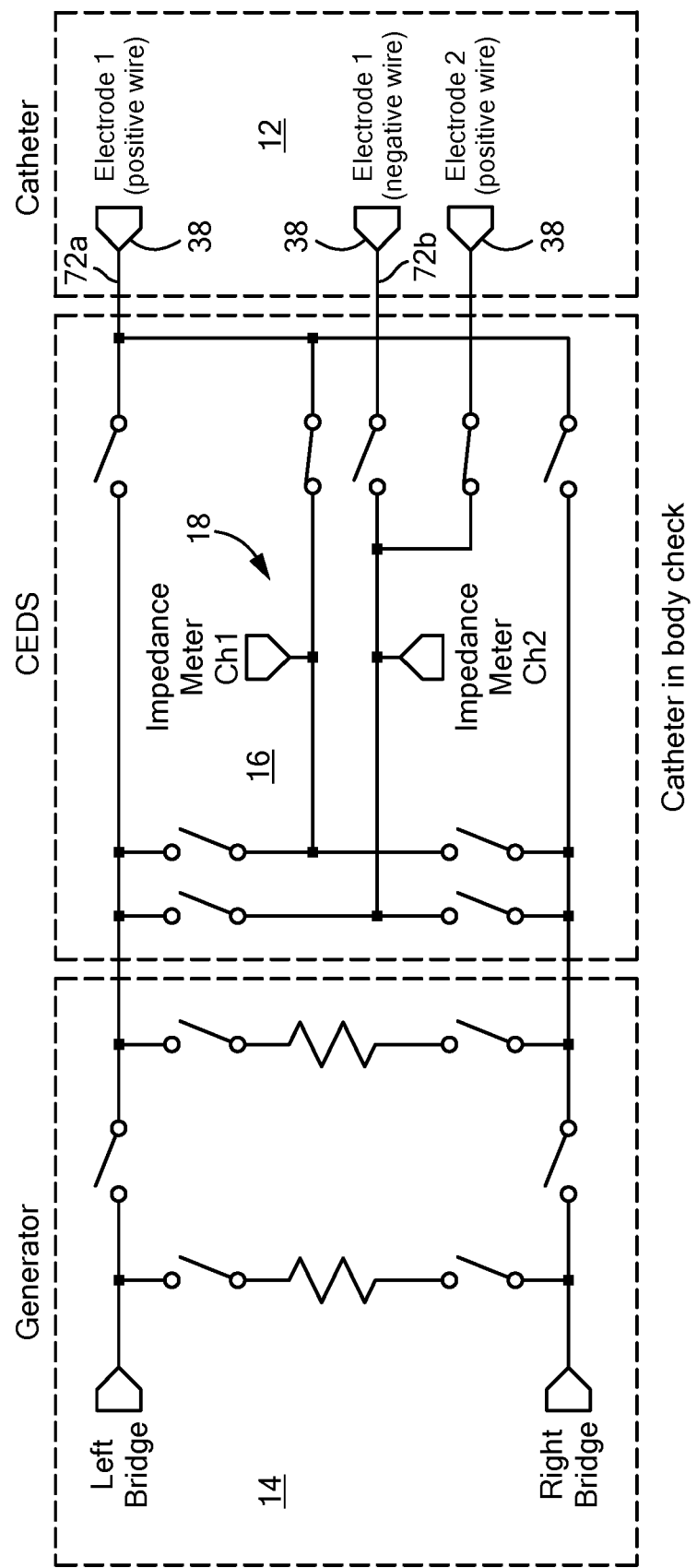
FIG. 16 shows a simplified diagram of relay configurations used to verify device-in-body integrity.

FIG. 16 shows a simplified diagram of relay configurations used to verify device-in-body integrity. In this test, the system measures the impedance between two adjacent device electrodes 38. If the device 12 or its cable are damaged, the test will resolve a very high (in the case of open conductors) or very low (in the case of shorted conductors) impedance. If the device 12 is in air (instead of within the patient's body), the test will resolve a very high impedance. Otherwise, the system will resolve tissue impedance, which is typically approximately 150 ohms. If the test resolves an impedance outside a range of possible tissue impedance values, it will trigger a fault state. The exact range may vary based on catheter electrode size and configuration, but an exemplary range for a pulmonary vein ablation catheter (PVAC®, Medtronic AF Luxembourg S.A.R.L.) catheter may be approximately 40-300 ohms.

Figure 17:
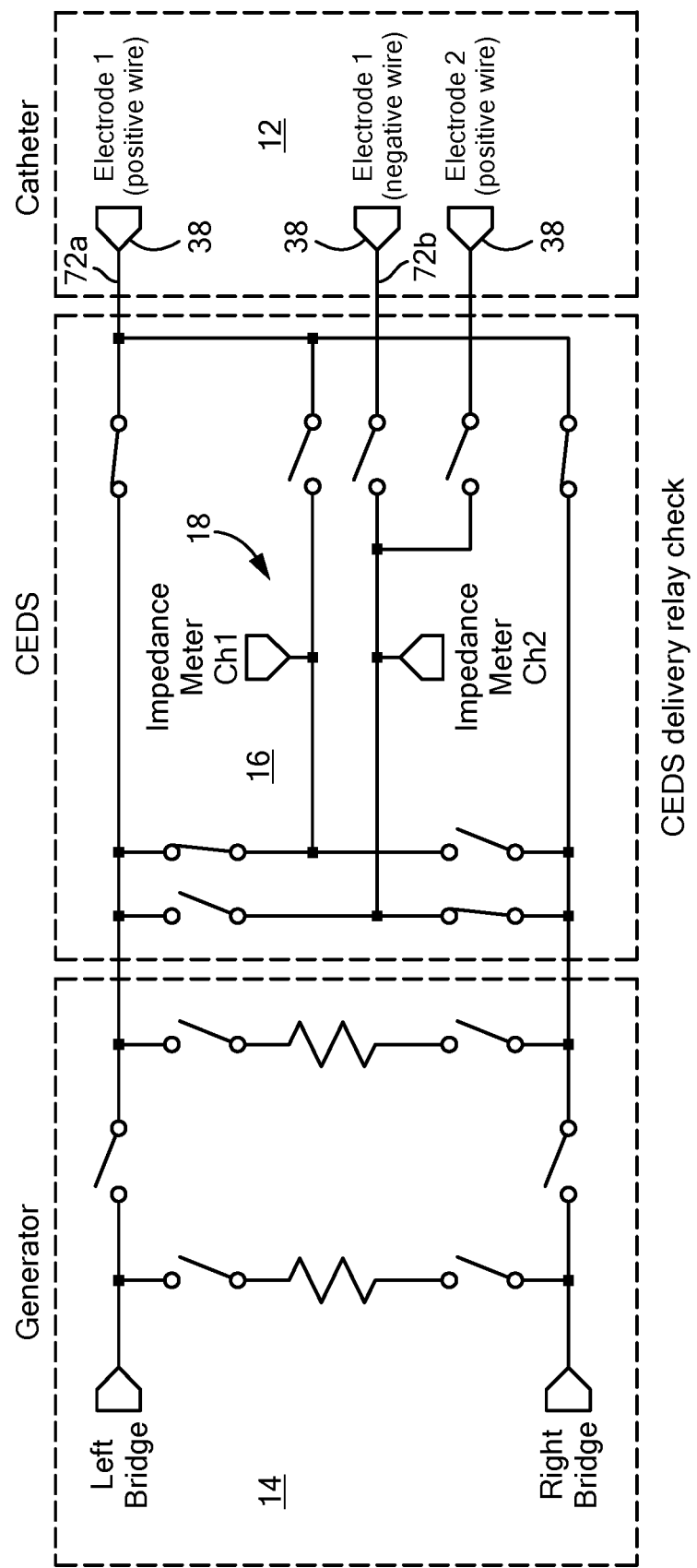
FIG. 17 shows a simplified diagram of relay configurations used to verify CEDS bridge relay integrity.

FIG. 17 shows a diagram of relay configurations used to verify CEDS bridge relay integrity. In this test, the system verifies that the energy delivery relays between the generator 14 and an electrode 38 being tested are operational by measuring the impedance of the relays. If the test is passed, the system will resolve a near short circuit. For example, the impedance of the relays are expected to be 0 ohms. However, accounting for measurement error and non-ideal components, the system may determine CEDS bridge relay is compromised if the impedance measurements are above approximately 10 ohms to approximately 30 ohms.

Figure 18:
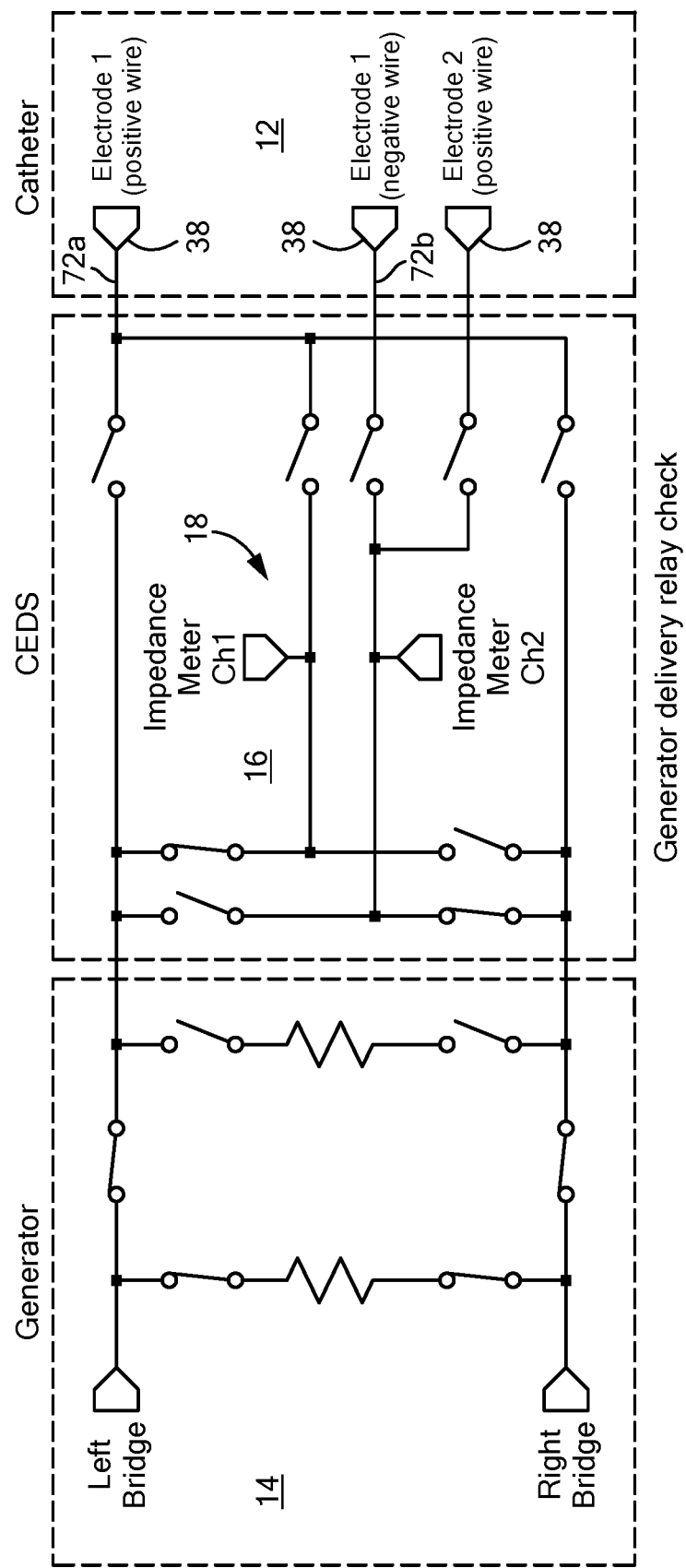
FIG. 18 shows a simplified diagram of relay configurations used to verify generator interlock relay integrity.

FIG. 18 shows a diagram of relay configurations used to verify generator interlock relay integrity. In this test, the system verifies the pathway back to the H bridge 54 is intact. If the test is passed, the system will resolve the impedance of the test load plus cabling between the CEDS 16 and the generator 14.

Figure 19:
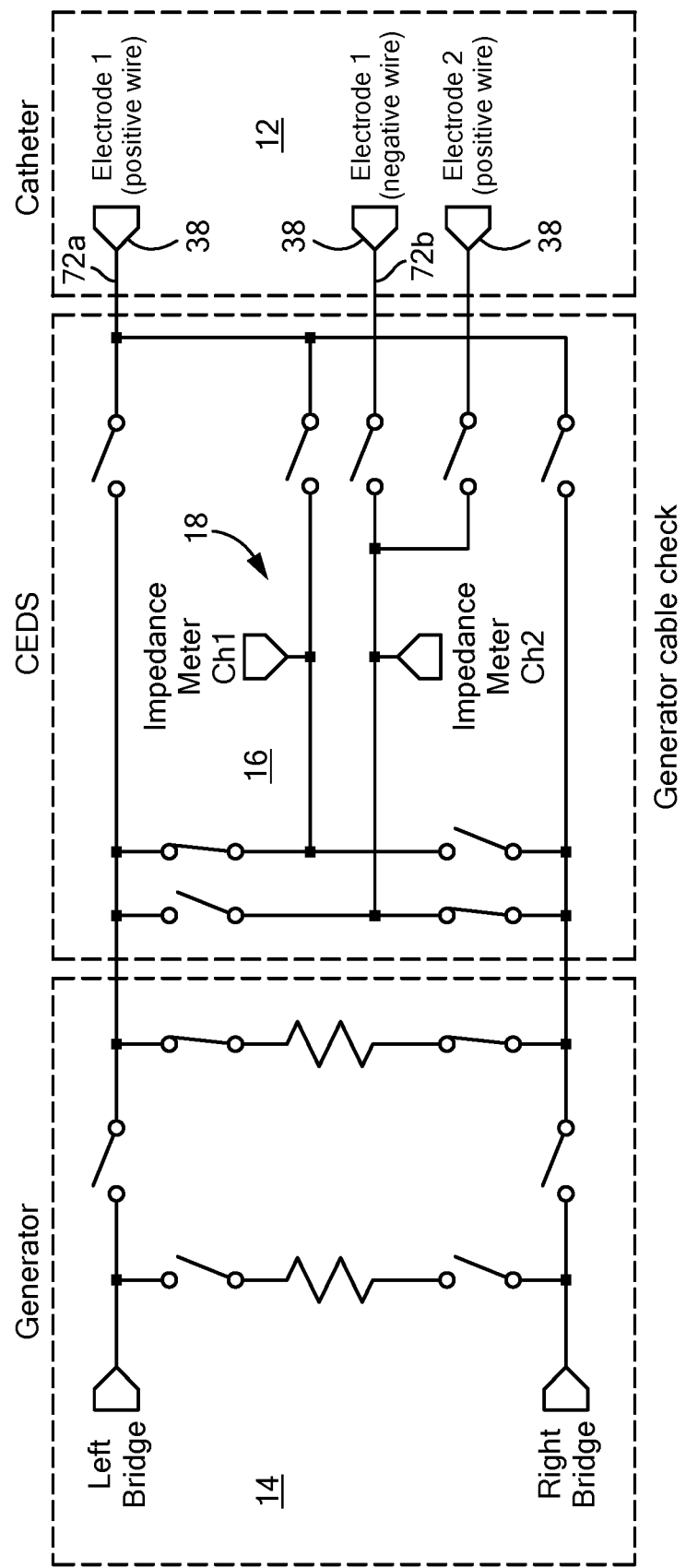
FIG. 19 shows a simplified diagram of relay configurations used to verify CEDS-generator cable integrity.

FIG. 19 shows a diagram of relay configurations used to verify CEDS-generator cable integrity. If the generator interlock relay test is passed, the CEDS-generator cable integrity test may not be required. If, on the other hand, the generator interlock relay test is failed, this test may determine whether the failure is the result of cabling or a generator relay. If the cabling between the CEDS 16 and generator 14 is intact, this test will resolve the impedance of the test load plus cabling. Otherwise, the system will resolve an open circuit.

Figure 20:
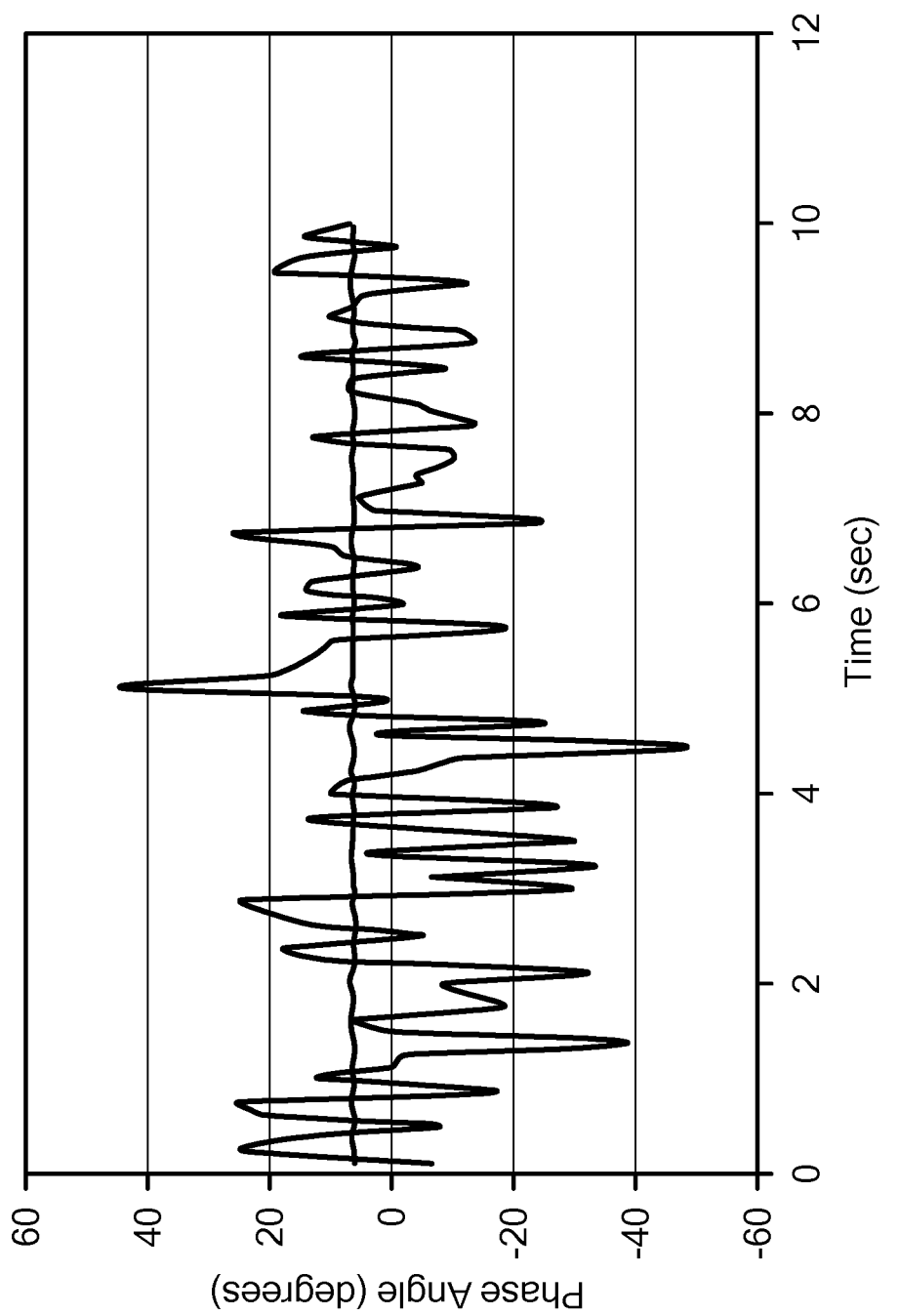
FIG. 20 shows an exemplary comparison between phase angle of a normal electrode pair and a faulty electrode pair.

Additionally, the phase angle associated with the impedance, or the difference between the voltage and the current, may be used to assess device and/or system integrity. For example, as the wire insulation in a system cable breaks down, the capacitance of the cable changes and this is reflected in a phase angle change in the device. The generator processing circuitry 44 and/or the CEDS processing circuitry 62 may monitor impedance phase angle during a treatment procedure and compare it to a predetermined threshold value or range. The comparison may be based on an instantaneous phase angle measurement and its associated threshold value and/or a phase angle over time measurement and its associated threshold value. As a non-limiting example, a threshold phase angle at 100 kHz may be between approximately 5 and approximately 20 degrees. If the processing circuitry detects a phase angle that is outside this threshold range, the system may alert the user of a potential system and/or device integrity issue. Additionally or alternatively, the processing circuitry may monitor impedance phase angle for each of the plurality of electrodes 38 and compare them to each other. For example, the system may alert the user of a potential system and/or device integrity issue if there is a high degree of variability between electrodes 38 or electrodes pairs (that is, if phase angle associated with one or more electrodes is greater or less than an average phase angle value across all electrodes), similar to the temperature measurement pathway integrity check. FIG. 20 shows an exemplary comparison between phase angle of a normal (unbroken) electrode pair, indicated by the line having a substantially constant value, and a faulty electrode pair, indicated by the erratic line.

Referring again to FIG. 7, once the checks in the second step 302 are performed and passed, energy delivery may still not proceed until synchronized with the R wave portion of myocardial depolarization (third step 203 in FIG. 7). High-voltage vacuum relays may disconnect the device 12 from external electrophysiology equipment and connect it to the generator's voltage output. However, R waves must arrive at a stable rate or the generator 14 will prevent the delivery of treatment energy to the device 12. For example, if there is a greater difference between a threshold time duration and the time between the last predetermined number of R waves, the generator 14 will prevent the delivery of treatment energy to the device 12. Similarly, if R waves arrive faster than the threshold time duration, or if it takes longer than a threshold time duration for an R wave to arrive, delivery of treatment energy will be prevented until the heart rate returns to normal.

After R-wave synchronization is complete, the delivery relays may be configured in the fourth step 204 to transition between a sensing mode (for example, in order to perform the pre-checks of the second step 202) and a treatment energy delivery mode.

If the various integrity tests are passed, the generator 14 may then permit the delivery of treatment energy to the device 12 in the fifth step 205. The treatment energy may be in the form of waveforms, which may be generated using reconfigurable logic in the generator 14. The generator 14 may be able to generate precisely timed treatment waveforms according to the selected treatment profile. Waveform timing and voltage can be changed without modifying firmware, or entirely new waveform shapes can be rapidly prototyped. Any or all of the integrity checks disclosed herein may be performed before, during or after the delivery of treatment energy. Further, if the integrity checks indicate a fault condition, one or more of the primary or secondary safeguards discussed above with reference to, for example, FIG. 6, will be engaged.

During delivery the system may also monitor for several fault conditions. One such fault condition is excessive charge delivery, which is detected using an integrating current monitor. Current passing through each half bridge may be monitored and mathematically integrated in real time according to the equation:

$$Q = \int_{T_1}^{T_2} i(t) dt \qquad (1)$$

where the current i(t), having flowed from each half bridge during a period presenting potential patient hazard between times $T_1$ and $T_2$ accrues to a charge, Q, which is then compared by an instantaneously responding electronic comparator circuit to an a priori known safe limit. If the charge Q exceeds the safe limit during that potential hazard period, the electronic comparator circuit may respond to the excessive charge and trigger and immediate termination of treatment energy by turning off a plurality of supplemental transistors in the generator 14. The monitor circuit will necessarily limit the time between times $T_1$ and $T_2$ to a short integration period.

Figure 9:
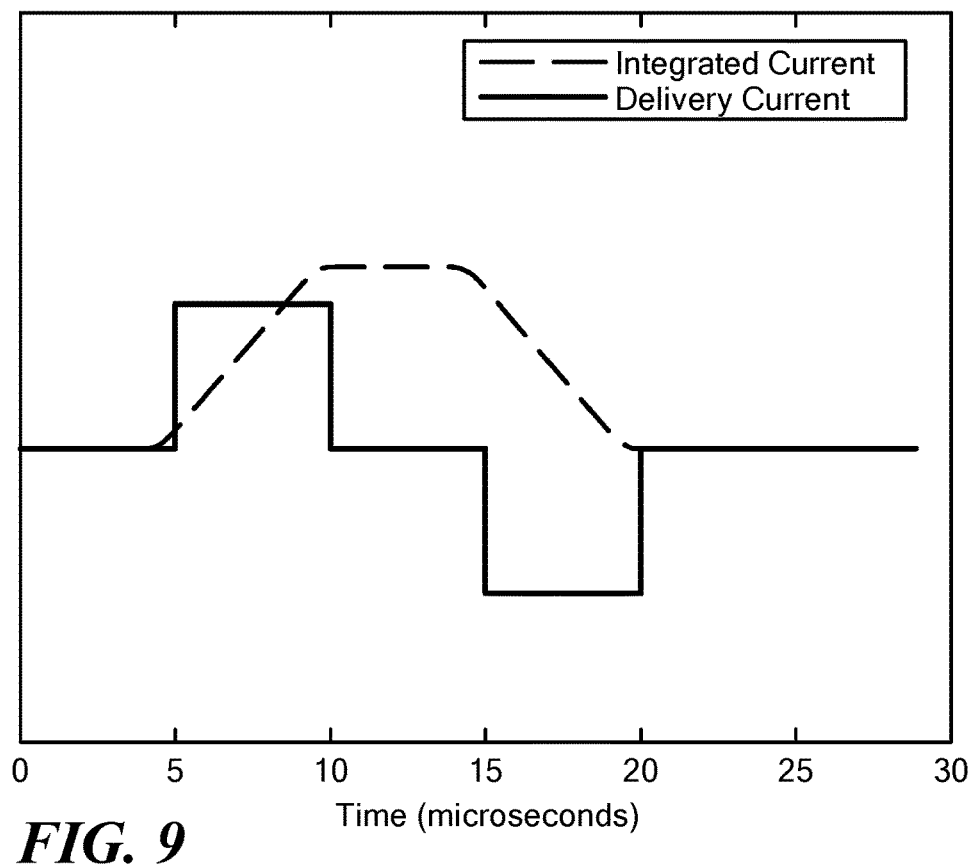
FIG. 9 shows a comparison of a delivery current and an integrated current over time with a correct/nonfaulty biphasic pair.
Figure 10:
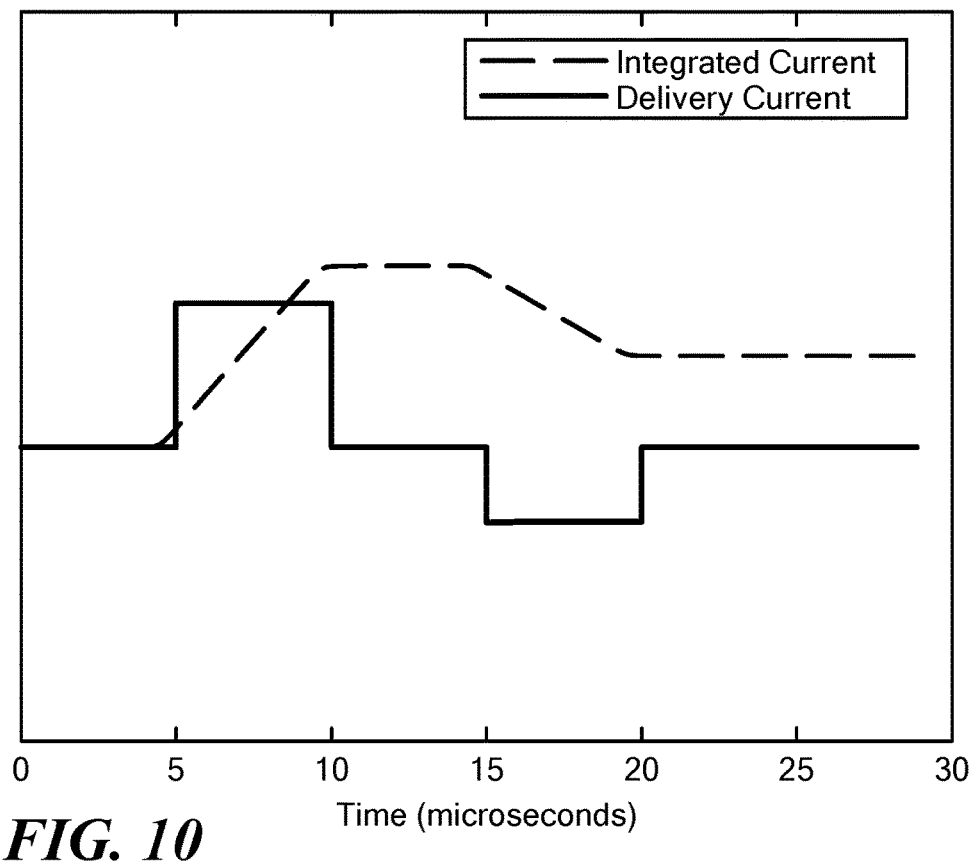
FIG. 10 shows a comparison of a delivery current and an integrated current over time with a pulse amplitude imbalance.
Figure 11:
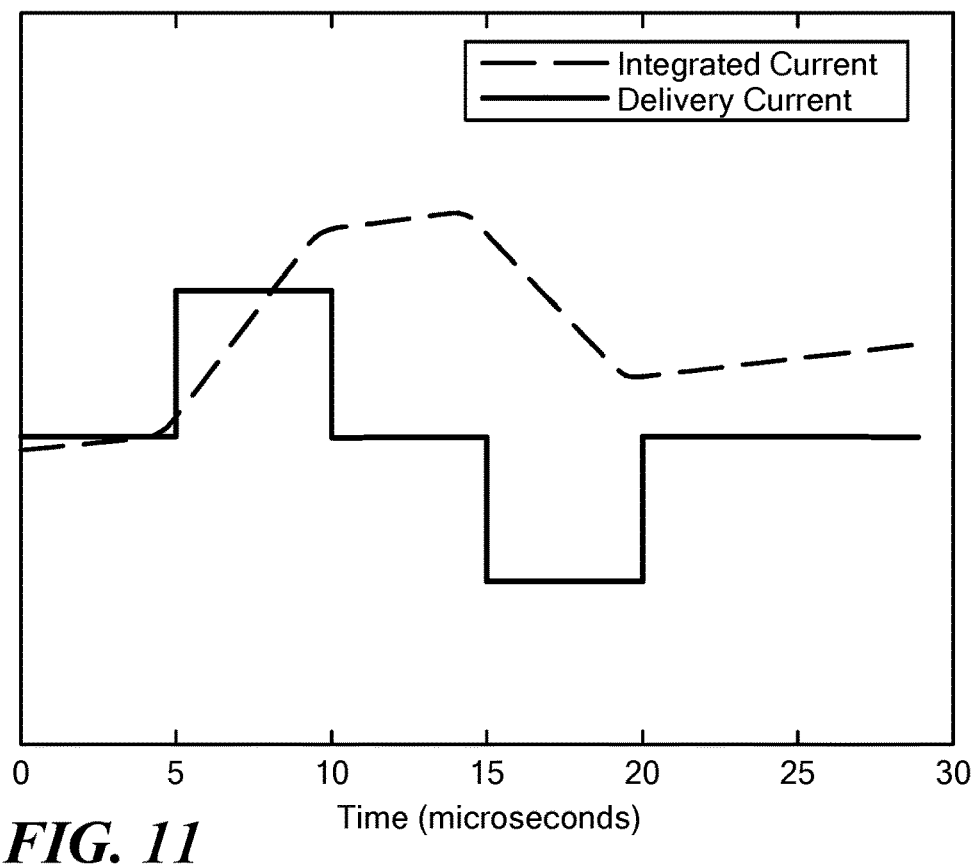
FIG. 11 shows a comparison of a delivery current and an integrated current over time with a current leak.
Figure 12:
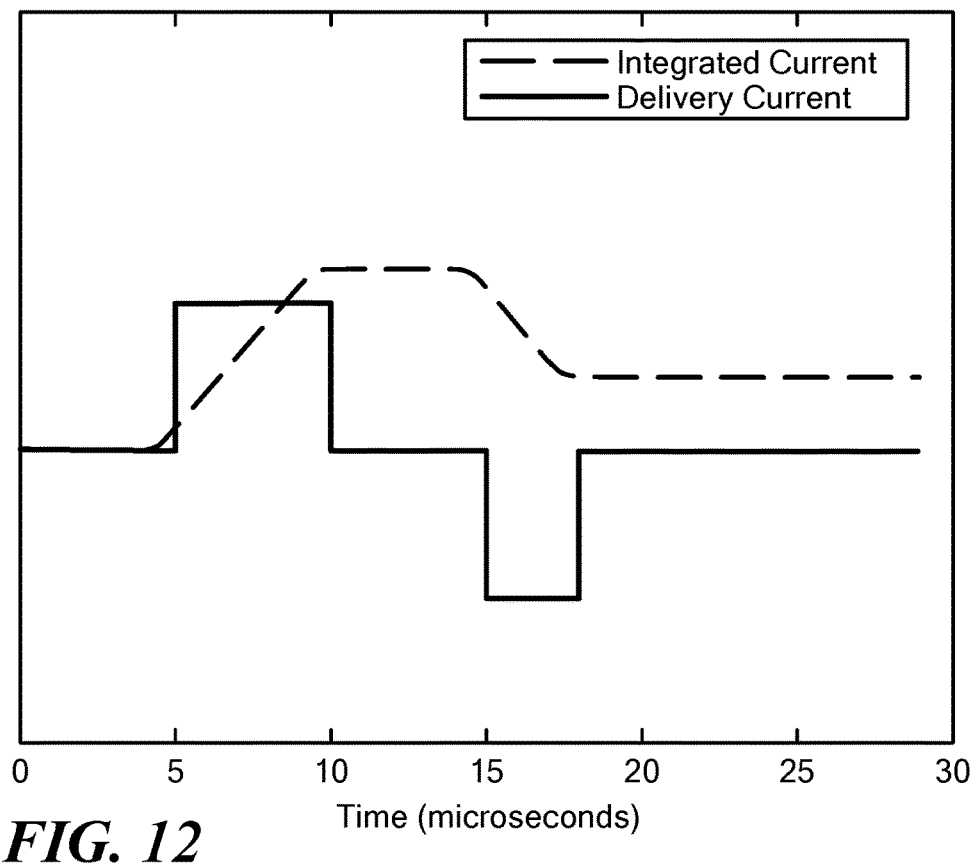
FIG. 12 shows a comparison of a delivery current and an integrated current over time with a pulse width imbalance.

The exact integration time is dictated by the range of pulse timing parameters available, since both halves of the biphasic pulse must be included in the integration. An integration time that is too short will not capture an entire biphasic pulse pair and is thus prone to false positive fault determinations. Integration times that are too long will allow more noise to be integrated into the result, which may cause false positives. A typical integration period may be on the order of 35 microseconds, which can support pulse widths as high as 12 microseconds, or pulse repetition rates as low as 60 microseconds. The integral of a completed biphasic PFA pulse is zero, as shown in FIG. 6. However, normal/non-faulty deliveries cause significant non-zero integral values during the course of the pulse. Thus, the fault signals must only be sampled after a pulse is complete. Included in FIGS. 7-9 are examples of three types of charge faults that may occur during delivery. FIG. 10 shows a pulse amplitude imbalance, FIG. 11 shows a current leak, and FIG. 12 shows a pulse width imbalance.

Two other types of fault that can be detected during delivery are excessive or insufficient current amplitude. Excessive amplitude may indicate a damaged device 12 or generator 14, or may be caused by an external object such as a guide wire shorting out catheter electrodes 38. Such a short condition may also occur if the multi-electrode array were to become compressed or distorted, such that the two electrodes having opposite polarities came into very close proximity or direct contact with one another. Insufficient amplitude may also indicate a damaged device 12 or generator 14, or may be caused by a partially or non-deployed device 12. FIG. 20 shows a current monitor and vertical current monitor circuit (which may also be referred to as a "current sense circuit") 80. This circuit 80 may appear twice in the generator 14, one on each bridge output (with the sense resistor R1 of FIG. 20 being shown as R1 in FIG. 8. The same configuration of R1 of FIG. 20 may also be included at R2 in FIG. 8). As shown in FIG. 20, the detector circuit is configured as a differential current-sense amplifier whose differential outputs are routed to a pair of comparators 82, with one comparator 82a receiving the amplifier's positive output and the other comparator 82b receiving the amplifier's the negative output. In this way the trip threshold applies to current in either the positive or negative direction. The processing circuitry 44 may be configured to control and set, with a digital-to-analog converter (DAC), the magnitude of the threshold.

This circuit 80 may be configured to establish an in-treatment current threshold amount and detect either excess or insufficient current relative to the in-treatment current threshold amount, and redundant hardware in the generator 14 may allow both conditions to be monitored simultaneously with excess current being monitored on one half bridge 54a and insufficient current being monitored on the other half bridge 54b. As a non-limiting example, the circuit 80 may be configured to measure instantaneous current values at any given point during the integration period and to measure or determine a peak current value for the integration period. Further, the circuit 80 may be configured to compare either or both an instantaneous current value and the peak current to the in-treatment current threshold. In the case of excessive amplitude, an absolute, time-invariant threshold may be set, with current exceeding this threshold for any length of time indicating a fault. Thus, the comparator 82 output can be used as a rising-edge-active trigger for the fault-response circuitry. A pair of comparators 82a, 82b is used in order to sense both positive and negative current (shown as I+ and I− in FIG. 20). Determining there is insufficient current may be more complicated, since nominal current output is zero (0) for the majority of the waveform. Thus, detecting insufficient current necessitates sampling the comparator's 82 output synchronous with a treatment pulse. The sampled output can then be used as an active-low fault indication. If a faulty current is detected, the system may then enter the fault-response state as shown and described in FIG. 6.

Figure 21:
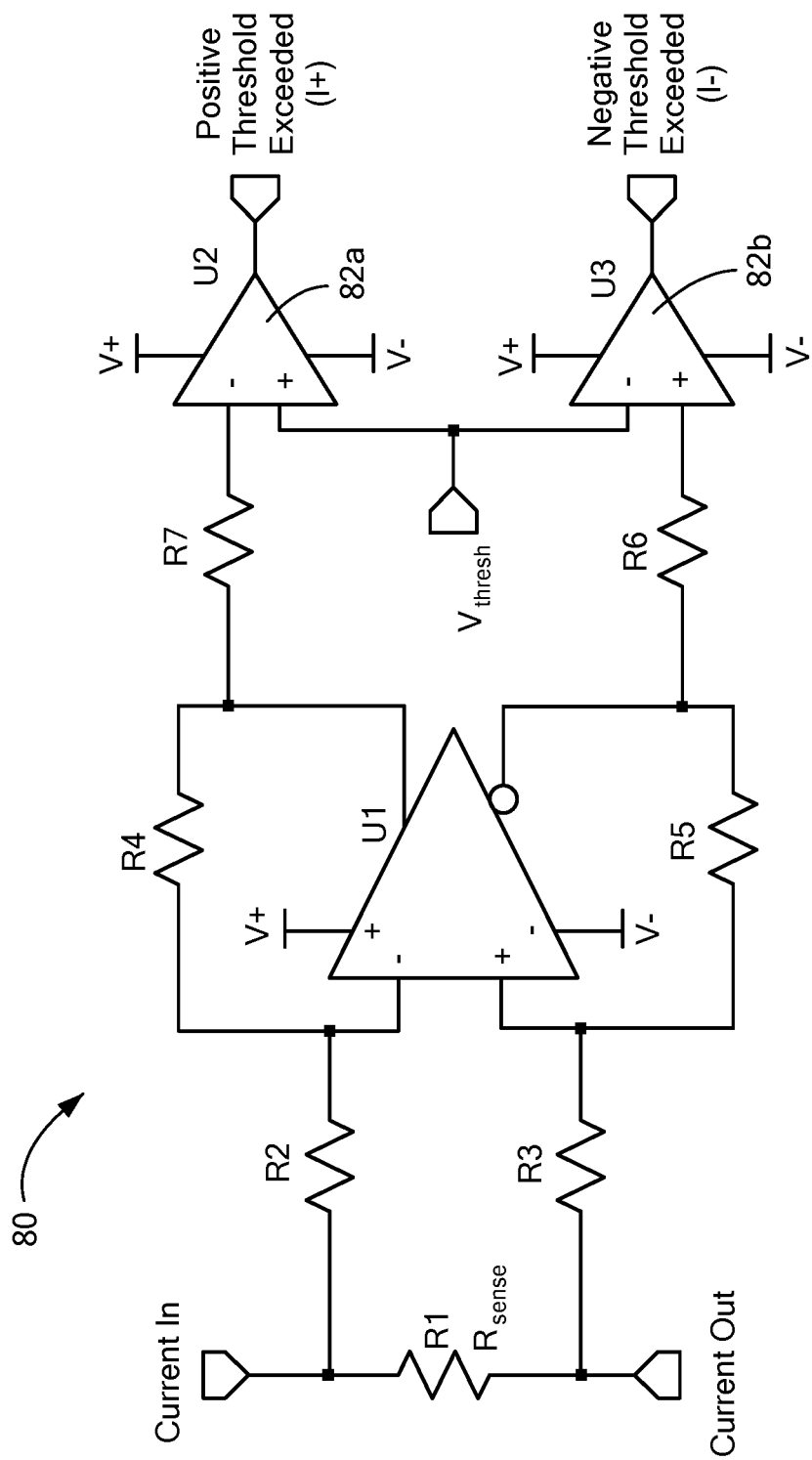
FIG. 21 shows a diagram of a current monitor and vertical current monitor circuit.

The final type of delivery fault detector detects vertical current in the H bridge 54. As shown in FIG. 2, under normal conditions current flows through the patient via either Q1 and Q4, or Q3 and Q2. Current flowing simultaneously through both Q1 and Q2 or Q3 and Q4 is known as "vertical current" and presents a risk of damaging the H bridge 54. An additional four current monitors (as shown in FIG. 20) may be included to detect vertical current before damage occurs. Current may be monitored as it enters and exits each leg of the H bridge 54, across R3, R4, R5, and R6 in FIG. 5. For simplicity, the monitor measuring Q1 is referred to as VC1. Likewise, the monitor measuring Q2 is referred to as VC2, and so on. If either of a detector's positive or negative comparators 82 are logic high, that monitor is said to be tripped or set. Current flow through Q1 and Q2 should be mutually exclusive, as should flow through Q3 and Q4, and thus under normal circumstance either VC1 or VC2 could be tripped, but not both. Similarly, either VC3 or VC4 could be tripped under normal operation but not both. If both VC1 and VC2 or both VC3 and VC4 are tripped, then a vertical current fault is raised. A diagram of the vertical current fault determination logic 86 is shown in FIG. 21.

In the sixth step 206, the peak delivery current may be recorded during and/or after the delivery of treatment energy to assess lesion quality using a peak and hold current monitor 88 as shown in FIG. 30. The arrow shown at the circled letter A in FIG. 30 represents the patient current ($I_{patient}$), which may be between approximately 5 amperes (A) and 40 A. The patient current, $I_{patient}$, or the current going to and returning from electrodes engaged with the patient's tissue, may be converted to a voltage with a sufficient bandwidth (for example, of approximately 200 MHz) by an amplifier 90. The positive output of the amplifier 90 may be used to monitor positive-going pulses (pathway marked by the circled letter B in FIG. 30) while the amplifier's negative output may be used to drive a mirror circuit (not shown) to monitor the negative-going pulses. When the patient $V_{in}$ signal exceeds a wiper signal of a digital potentiometer 94, output from a comparator 92 is positive and applies an enable signal to the digital potentiometer 94 (pathway marked by the circled letter C in FIG. 30). The clock signal is then applied to the digital potentiometer 94 to set the sampling rate. As a non-limiting example, the sampling rate may be approximately 500 KHz assuring that five samples are taken for a 3 µsec-wide pulse (indicated by the circled letter D in FIG. 30). For example, the clock may have jitter to ensure asynchrony with the sampled signal. Once the digital potentiometer signal equals the positive amplifier output, the comparator's output goes low and the digital potentiometer 94 will hold its last peak value at the wiper (pathway indicated at the circled letter E in FIG. 30). This value may then be referred to, such as on one or more system displays, as the treatment delivery procedure's peak patient current.

In this circuit, the current is continually sampled during the treatment procedure and the highest recorded current value is retained unless a subsequent value is higher than an earlier recorded value. Although both the fault detector logic 86 discussed above and the peak and hold monitor 88 may be used, the peak and hold monitor method may be better suited as a current value recorder than the fault detector discussed above. Although the fault detector 86 is very useful for terminating a harmful energy delivery, it compares real-time peak current against a threshold, but then may disguise the actual current unless it happens to reach the threshold, and only in that case can it be known that the current actually reached the threshold. In contrast, the peak and hold current monitor 88 will always render and report the peak current during the treatment energy delivery procedure. Furthermore, typically used on-board pulsed field instrumentation, such as a Nyquist sampling oscilloscope, may add substantial complexity, cost, and size to the energy delivery generator. However, the system shown in FIG. 30 may be able to assert the episodic peak delivered current simply by use of an amplifier 90 providing adequate step response, and rendering its output to a comparator device 92 of which output continues to instruct a digital potentiometer 94 to increase its output—now a threshold—at the reference pin of the comparator 92. While the incoming sampled voltage to the comparator 92 exceeds the reference threshold set by the digital potentiometer 94, the system will continue to "ratchet upward" until the digital potentiometer's output reaches the most recent peak value, and thus remain stable in a hold state until the value is rendered and reported to the user. Given the "upward or hold" operation of the peak and hold monitor 88, two peak and hold monitors optionally may be used such that monitor is dedicated for positive-going pulses in a treatment energy waveform and a second monitor, with its output inverted, monitors negative-going pulses in the treatment waveform. Then, the peak and hold monitor 88 may record and communicate this value to the user. An optimum peak delivery current may be between approximately 5 A and approximately 40 A ($I_{patient}$); however, the optimum peak delivery current may depend on the characteristics of the delivery device 12, such as the configuration of the treatment element 34, number and configuration of electrodes 38, the quality of contact between tissue and the electrodes 38, and the like. The sixth step 206 may also include recording the peak temperature from each of the thermocouples 63 before, during, and/or after the delivery of treatment energy and comparison to a pre-determined threshold. Additionally or alternatively, the system may include additional thermocouples or other types of temperature sensors (for example, proximate an energy delivery pathway and not associated with the electrodes 38) that may record temperature measurements, such as an ambient room temperature and/or temperature(s) in one or more parts of the system other than at the electrodes 38. Any of these measurements may be used as a baseline temperature for comparison with in-treatment or post-treatment temperature measurements. In other words, a pre-treatment temperature measurement from each thermocouple or other temperature sensor may be recorded to determine a baseline temperature (although not shown on the flow chart of FIG. 7). After (for example, immediately after) a delivery of treatment energy, a post-treatment temperature measurement may be recorded and compared to the pre-treatment measurements to calculate a temperature difference for each thermocouple. If the temperature difference and/or a measure of the absolute temperature post-energy delivery for any thermocouple exceeds a threshold value, the processor 44 may determine a fault condition exists. As a non-limiting example, peak temperatures of above approximately 50° C. may be considered the threshold temperature for thermal damage to be caused to the tissue. If such peak temperatures persist for less than five seconds, the threshold for thermal damage may be increased to a second threshold temperature, for example, approximately 60° C. Of concern in such cases of high peak temperatures is the formation of thermally denatured protein deposits on the electrodes that have the potential to embolize. Thus, if these temperature thresholds are exceeded, the processor 44 may terminate the delivery and/or prevent the further delivery of treatment energy. Additionally or alternatively, the processor 44 may cause a reduction in output voltage and/or number of pulses to reduce the peak temperatures to less than the pre-established threshold. Further, the system 10 may prevent the delivery of treatment energy unless and until a user clears the warning. This safeguard may enhance safety of the system 10 by avoiding overtemperature conditions.

In the seventh step 207, the system 10 may communicate various system reports, measurements, recommendations, summaries, and/or other procedure information to the user, such as by the one or more displays 46.

Figure 24:
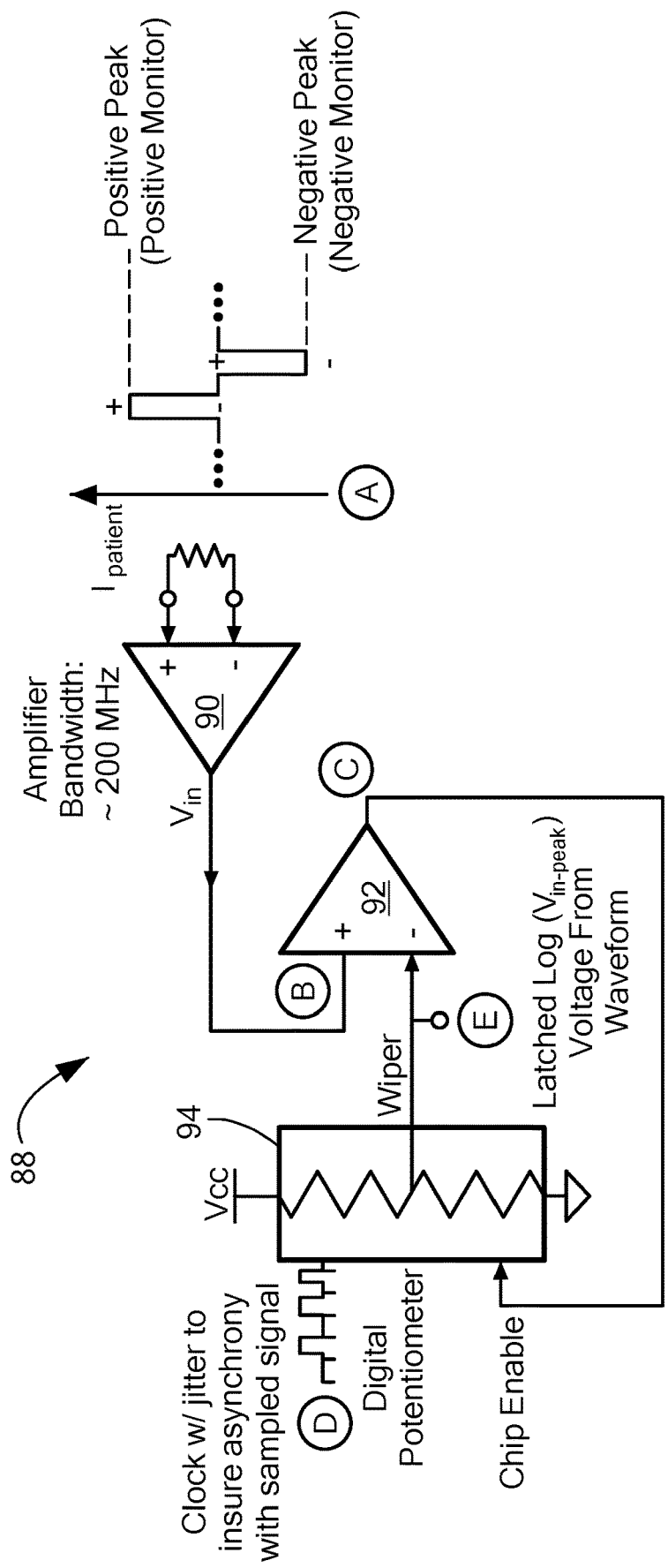
FIG. 24 shows an exemplary monitor for recording a peak delivery current for lesion quality assessment.
Figure 25:
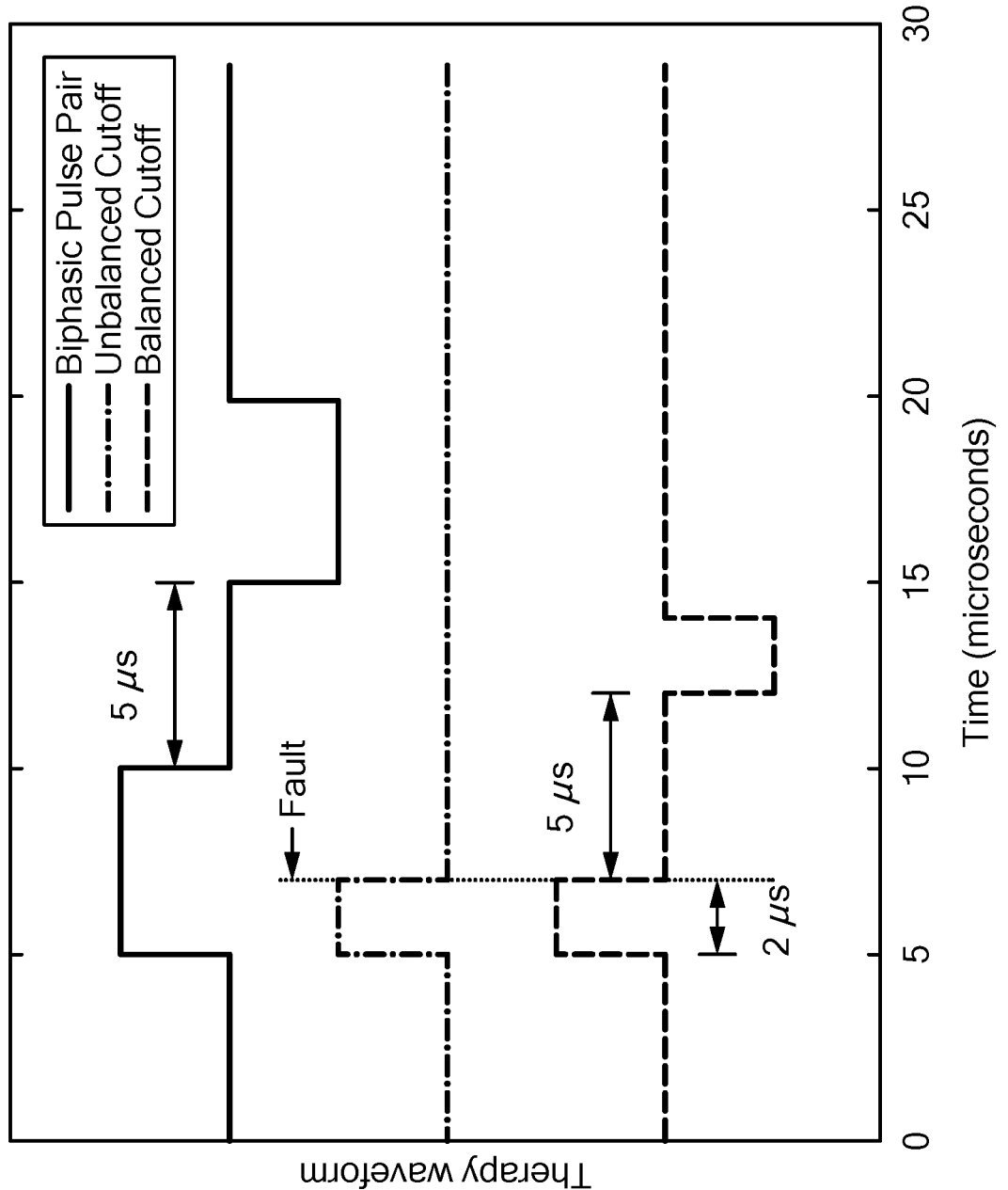
FIG. 25 shows a comparison between a full biphasic pulse pair, an immediate shutoff at 2 microseconds, and the effect of a fault triggering a balanced shutoff.

Referring now to FIG. 24, a comparison between a full biphasic pulse pair, an immediate shutoff, and an effect of a fault triggering a balanced shutoff is shown. Unwanted muscle stimulation can occur when net electrical charge is delivered to the heart. Pulsed field ablation uses short, closely spaced biphasic pulses to minimize net charge delivered. Disrupting this pattern may result in excessive charge delivery and muscle stimulation. However, if a fault state occurs, the delivery of treatment energy must be cut off quickly to ensure patient safety. The tests described above may be conducted continuously or at intervals during the delivery of treatment energy. If a fault is detected, the system 10 may enact the electrical and/or electromechanical safeguards discussed above. For example, as shown in FIG. 24, the delivery of treatment energy may be immediately terminated when a fault is detected. Alternatively, the charge delivery may be balanced before being terminated. Pulses of opposite polarities tend to cancel each other's charge, so the balanced cutoff may allow the biphasic pulse to complete both phases before terminating the delivery of treatment energy. Further, if the fault is detected in the first half of a biphasic pair, the generator 14 may shorten both phases to more quickly balance charge and disengage from the patient. A non-limiting graphical representation of a comparison between a biphasic pulse pair, the effect of an immediate shutoff at 2 microseconds, and the effect of a fault at 2 microseconds triggering a balanced shutoff.

As will be appreciated by one of skill in the art, certain concepts described herein may be embodied as a method, data processing system, and/or computer program product. Accordingly, these concepts described herein may take the form of an entirely hardware embodiment, an entirely software embodiment or an embodiment combining software and hardware aspects. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of delivering treatment energy from a medical system, the medical system including a device having a plurality of electrodes, an energy generator, and a catheter electrode distribution system (CEDS), the method comprising:
performing a plurality of pre-checks, the plurality of pre-checks including:
recording a temperature measurement from each of the plurality of electrodes and determining a pre-check fault condition exists when at least one of:
the recorded temperature measurements differ from each other by more than a threshold amount; and
at least one of the recorded temperature measurements is less than a threshold temperature;
recording an impedance measurement from each of the plurality of electrodes and determining a pre-check fault condition exists when at least one of:
at least one of the recorded impedance measurements is outside of a threshold impedance range; and
a bipolar impedance between adjacent electrodes of the plurality of electrodes is outside of a threshold bipolar impedance range;
measuring a current passing through a monitor within the energy generator within each of a long integration period and a short integration period, calculating an integrated current, and determining a pre-check fault condition exists when the measured current is greater than a threshold integrated current amount;
determining whether at least one of a first electrode wire and a second electrode wire are disconnected from the CEDS and determining a pre-check fault condition exists when at least one of the first electrode wire and the second electrode wire are disconnected from the CEDS; and
initiating a delivery of treatment energy from the energy generator when no fault conditions are determined to exist,
wherein the CEDS includes a first pullup resistor connected to the first electrode wire and a second pullup resistor connected to the second electrode wire, the first pullup resistor being driven at a first voltage and the second pullup resistor being driven at a second voltage, the first and second voltages being different.

2. The method of claim 1, further comprising:
after the initiation of the delivery of treatment energy, determining whether at least one of the first electrode wire and the second electrode wire are disconnected from the CEDS and determining a delivery fault condition exists when at least one of the first electrode wire and the second electrode wire are disconnected from the CEDS; and
initiating at least one of an electronic safeguard and an electromechanical safeguard when the delivery fault condition is determined to exist.

3. The method of claim 2, wherein the electronic safeguard includes at least one of a primary electronic safeguard and a redundant electronic safeguard and the electromechanical safeguard includes at least one of a primary electromechanical safeguard and a redundant electromechanical safeguard.

4. The method of claim 3, wherein:
the primary electronic safeguard includes terminating the delivery of treatment energy from the energy generator by turning off a plurality of delivery transistors in the energy generator;
the redundant electronic safeguard includes terminating the delivery of treatment energy from the energy generator by turning off a plurality of supplemental transistors in the energy generator;
the primary electromechanical safeguard includes interrupting the delivery of treatment energy from the energy generator by activating at least one relay in the energy generator; and
the redundant electromechanical safeguard includes interrupting the delivery of treatment energy from the energy generator by activating at least one relay in the CEDS.

5. The method of claim 1, further comprising:
after the initiation of the delivery of treatment energy, measuring a current passing through a monitor within the energy generator within each of a long integration period and a short integration period, measuring the current including measuring at least one instantaneous current during each of the long integration period and the short integration period and a peak current during each of the long integration period and the short integration period;
establishing an in-treatment threshold current amount; and
determining a fault condition exists when at least one of the measured at least one instantaneous current and peak current is one of greater than the in-treatment threshold current amount and less than the in-treatment threshold current amount.

6. The method of claim 1, wherein each of the plurality of electrodes includes a thermocouple, the thermocouple having a first wire and a second wire, each of the first and second wires being in communication with the CEDS.

7. The method of claim 6, wherein after the initiation of the delivery of energy treatment, the determination of a fault condition includes:
recording a thermocouple voltage from each thermocouple;
comparing the recorded thermocouple voltage from each thermocouple to a first threshold voltage; and determining that there is a fault condition in only the first wire of the thermocouple from which a recorded thermocouple voltage is greater than the first threshold voltage.

8. The method of claim 7, further comprising:
determining whether there is a fault condition by:
comparing the recorded thermocouple voltage from each thermocouple to a second threshold voltage; and
determining that there is a connection fault condition in both the first wire and the second wire of the thermocouple from which a recorded thermocouple voltage is greater than the second threshold voltage.

9. The method of claim 8, further comprising:
determining whether there is a fault condition by:
comparing the recorded thermocouple voltage from each thermocouple to a third threshold voltage; and
determining that there is a fault condition in only the second wire of the thermocouple from which a recorded thermocouple voltage is less than the third threshold voltage.

10. The method of claim 1, wherein the processing circuitry and the energy generator further include an integrating current monitor having a short integration time and a high-energy delivery circuit having a first half bridge and a second half bridge, determining there is a fault condition when there is an excessive charge delivery, the processing circuitry being configured to determine whether there is an excessive charge delivery by:
monitoring a current passing through the first half bridge and the second half bridge;
integrating the current in real time during the delivery of treatment energy;
determining an integral value of the current; and
determining the fault condition exists when the integral value is a value other than zero.

11. The method of claim 1, wherein the threshold amount is greater than 2° C.

12. The method of claim 1, wherein the threshold temperature is less than 35° C. or greater than 40° C.

13. The method of claim 1, wherein each electrode in the plurality of electrodes further comprises a thermocouple and the plurality of pre-checks further includes:
recording a temperature measurement from each of the plurality of electrodes and determining a pre-check fault condition exists when the rate of temperature change is greater than a threshold rate.

14. The method of claim 1, wherein the threshold impedance range is between 50-500 Ohms.

15. The method of claim 1, wherein the threshold bipolar impedance range is between 40-300 Ohms.

16. The method of claim 1, determining whether the pre-check fault condition exists further comprises:
at least one of the first and second wires being intermittently connected to the CEDS.

17. The method of claim 1, wherein calculating the integrated current is based on the measured current passing through the monitor within the energy generator within each of the long integration period and the short integration period.

* * * * *